United States Patent
Kimoto et al.

(10) Patent No.: US 10,555,686 B1
(45) Date of Patent: Feb. 11, 2020

(54) REMOVING PARASITIC EFFECTS FROM BODY IMPEDANCE MEASUREMENTS WITH WRIST-WORN AND/OR OTHER DEVICES

(71) Applicants: Richard C. Kimoto, Fremont, CA (US); Thomas J. Sullivan, San Jose, CA (US); Paras Samsukha, San Jose, CA (US)

(72) Inventors: Richard C. Kimoto, Fremont, CA (US); Thomas J. Sullivan, San Jose, CA (US); Paras Samsukha, San Jose, CA (US)

( * ) Notice: Subject to any disclaimer, the term of this patent is extended or adjusted under 35 U.S.C. 154(b) by 612 days.

(21) Appl. No.: 15/201,115

(22) Filed: Jul. 1, 2016

Related U.S. Application Data

(60) Provisional application No. 62/187,705, filed on Jul. 1, 2015.

(51) Int. Cl.
*A61B 5/053* (2006.01)
*A61B 5/00* (2006.01)
*G01R 27/02* (2006.01)

(52) U.S. Cl.
CPC ............ *A61B 5/0531* (2013.01); *A61B 5/681* (2013.01); *A61B 5/053* (2013.01); *A61B 5/7203* (2013.01); *A61B 5/7225* (2013.01); *G01R 27/02* (2013.01)

(58) Field of Classification Search
CPC ..... A61B 5/0531; A61B 5/681; A61B 5/7203; A61B 5/7207; A61B 5/7225; A61B 5/053; G01R 27/02
See application file for complete search history.

(56) References Cited

U.S. PATENT DOCUMENTS

| | | | |
|---|---|---|---|
| 4,845,518 A | 7/1989 | Landwehr |
| 4,987,432 A | 1/1991 | Landwehr |
| 5,810,742 A | 9/1998 | Pearlman |
| 6,888,640 B2 | 5/2005 | Spina et al. |
| 7,457,660 B2 | 11/2008 | Ironstone et al. |
| 8,060,196 B2 | 11/2011 | Lippert et al. |
| 8,374,671 B2 | 2/2013 | Barnes |
| 8,583,215 B2 | 11/2013 | Lichtenstein |
| 8,836,345 B2 | 9/2014 | Bruinsma et al. |

(Continued)

OTHER PUBLICATIONS

"Non-Final Office Action", U.S. Appl. No. 15/201,119, dated Sep. 7, 2018, 16 pages.

*Primary Examiner* — Sean P Dougherty
(74) *Attorney, Agent, or Firm* — Kilpatrick Townsend & Stockton LLP

(57) ABSTRACT

Methods and devices for removing parasitic effects from body impedance measurements. Such parasitic effects can include parasitic coupling(s)/impedance(s) and/or parasitic coupling between the impedance measurement device and the body tissue being measured. In one approach, a drive current is controlled so as to control the voltage of a sense electrode to reduce a parasitic current. In another approach, different known capacitances are added to enable calculation of unknown electrode impedances. In another approach, a positive feedback loop is used to reduce error associated with a parasitic current of a voltage sensor used to measure resulting subject voltage. In another approach, sequential application of drive voltage to each electrode is used and resulting currents through all electrodes are measured and used to calculate body impedance.

22 Claims, 19 Drawing Sheets

(56) References Cited

U.S. PATENT DOCUMENTS

| | | |
|---|---|---|
| 2004/0077944 A1 | 4/2004 | Steinberg et al. |
| 2007/0276270 A1 | 11/2007 | Tran |
| 2011/0112430 A1 | 5/2011 | Karo et al. |
| 2011/0130676 A1 | 6/2011 | Murakawa et al. |
| 2013/0261470 A1 | 10/2013 | Allison et al. |
| 2014/0039341 A1 | 2/2014 | Bohorquez et al. |
| 2014/0257741 A1 | 9/2014 | Chupp |
| 2014/0289312 A1 | 9/2014 | Jafarifesharaki |
| 2016/0000385 A1 | 1/2016 | Petersen et al. |
| 2016/0113578 A1 | 4/2016 | Eom et al. |
| 2016/0157749 A1 | 6/2016 | Bohorquez et al. |
| 2016/0198977 A1* | 7/2016 | Eom .............. A61B 5/0537 600/384 |
| 2016/0256111 A1* | 9/2016 | Cheng ............ A61B 5/7203 |
| 2016/0374588 A1 | 12/2016 | Shariff et al. |
| 2017/0215745 A1* | 8/2017 | Felix .............. A61B 5/743 |
| 2017/0303814 A1* | 10/2017 | Van De Pas ...... A61B 5/7203 |
| 2017/0366213 A1* | 12/2017 | Camacho Perez ...... H04W 4/70 |
| 2018/0156660 A1* | 6/2018 | Turgeon ........... G01J 1/4204 |

* cited by examiner

REMOVING PARASITIC EFFECTS FROM BODY IMPEDANCE MEASUREMENTS WITH WRIST-WORN AND/OR OTHER DEVICES

CROSS REFERENCE TO RELATED APPLICATION DATA

The present application claims the benefit of U.S. Provisional Appln. No. 62/187,705 filed Jul. 1, 2015; the full disclosure which is incorporated herein by reference in its entirety for all purposes.

BACKGROUND

Fitness tracking devices, smart watches, and other wireless health monitoring devices have been found to be capable of sensing, recording, and transmitting a number of health-related information. These devices are now helping to track users' walking, running, and the like; to identify and track heart rate; and to encourage patients to remain active regularly throughout the day; often through the use of a relatively small, unobtrusive, wrist-worn device.

Along with monitoring of standard activity parameters, it may also be desirable to monitor bioelectrical signals (e.g., EKG, body impedance) in an easy-to-use ambulatory setting. Unfortunately, measurement of the desired relatively small signals from the heart often involve coupling expensive, temporary electrodes to a chest of a patient using gels and/or adhesives. While selected electrical health measurements can be obtained through skin of an individual's limbs using research or clinical measurement systems, the small amplitude of many of the signals of interest, the noise generated in the body and at the interface between the measurement system and body, the distance between (for example) the heart and the wrist, and the like have limited the monitoring of electrical signals from the body outside of the clinic and/or in the absence of large and expensive measurement systems.

Despite the limitations of existing technologies, impedance measurements may be used in a variety of different approaches for assessing the health of a subject. For example, bioelectrical impedance analysis (BIA) is a non-invasive technique that can be used to measure body composition in terms of percentage body fat. As another example, impedance cardiography (ICG) can use electrical and impedance signals to detect the properties of the blood flow in the thorax of a subject. The electrical and impedance signals can be processed to measure and calculate various hemodynamic parameters, such as heart rate, cardiac output, the amount of blood pumped by the left ventricle each heartbeat, the resistance to the flow of blood in the vasculature, peak acceleration of blood flow in the aorta, peak velocity of blood flow in the aorta, thoracic fluid content, the pre-ejection period (the time interval from the beginning of electrical stimulation of the left ventricle to the opening of the aortic valve), and left ventricle ejection time. As another example, Electrical Impedance Myography (EIM) is a non-invasive technique that can use the electrical impedance of individual muscles as a diagnostic tool for a number of neuromuscular diseases. EIM measures changes in muscle composition that occur during disease progression.

Impedance measurements can be made using a tetra-polar measurement method. Tetra-polar measurement methods may be more accurate than bi-polar measurement methods, but may suffer from parasitic impedances or coupling as the form factor of the measurement device gets smaller.

BRIEF SUMMARY

Methods and devices are described for removing parasitic effects from body impedance measurements. Such parasitic effects can include parasitic coupling(s)/impedance(s), such as parasitic coupling between the impedance measurement device and the body tissue being measured. As set forth below, a variety of different approaches are described and can be used alone or in any suitable combination. The approaches described herein can be used to correct at least a portion of impedance measurement error that may arise due to parasitic current losses, which may arise due to parasitic impedances and/or coupling, intentional and/or unintentional, between the impedance measurement device and the body tissue being measured. Such approaches are especially beneficial with regard to subject-mounted impedance measuring devices, which may be capable of continuous monitoring of the subject.

Thus, in one aspect, a first method is provided for measuring a body impedance of a subject. The first method includes propagating an alternating drive current through the subject between first and second drive current electrodes so as to control a voltage level of a first sense electrode relative to a reference ground voltage level via a feedback loop operatively connected between one of the drive current electrodes and the first sense electrode. One or more voltage levels of the subject resulting from the drive current are sensed via the first sense electrode and a second sense electrode. A body impedance value for the subject is calculated based on the drive current and the one or more sensed voltage levels.

Any suitable approach can be used for propagating the drive current so as to control the voltage level of the first sense electrode relative to the reference ground level. For example, the feedback loop can be configured to maintain the voltage level of the first sense electrode equal to the reference ground voltage level. Any suitable feedback loop can be used. For example, the feedback loop used can include an integrator having an integrator first input connected with the first sense electrode, an integrator second input connected to a ground having the reference ground voltage level, and an integrator output outputting a voltage level lower than the reference ground voltage level when the first sense electrode has a voltage level higher than the reference ground voltage level. The feedback loop can include a trans impedance amplifier (TIA) having a TIA first input connected to the integrator output, a TIA output, and a TIA second input connected with the TIA output. The TIA second input can be connected to said one of the drive electrodes. The feedback loop can include a first resistor connected between the first sense electrode and the integrator first input, a capacitor connected between the integrator first input and the integrator output, and a second resister connected between the TIA output and the TIA second input.

The first method can be used in conjunction with a subject-mounted device, which may be capable of continuous subject monitoring and/or have additional functionality beyond measuring the impedance of a portion of the subject. For example, the first and second drive current electrodes and the first and second sense electrodes can be coupled to a wrist-worn device. The body impedance value calculated can include a cross-body impedance of the subject. A cross-body impedance can be measured by propagating a measurement current across the thorax of a subject (e.g., through one of the subject's arms to the subject's other arm) and measuring a resulting voltage potential across the subject's thorax (e.g., between one of the subject's arms and the subject's other arm). The wrist-worn device can include an external case in contact with the user when the wrist-worn device is worn by the user. The external case can be connected to a ground having the reference ground voltage level. The wrist-worn device can include circuitry at least partially disposed within the external case. In many embodiments, the external case is configured to be worn on the wrist. The first and second drive current electrodes can be mounted on the external case and/or on a wrist band of the wrist-worn device. The first and second sense electrodes can be mounted on the external case and/or the wrist band. The body impedance value calculated can include a cross-body impedance of the subject. At least one of the electrodes can be configured to engage the wrist when the case is mounted thereon. At least one of the electrodes can be configured to be engaged by a finger of the patient, the finger being supported by another wrist of the subject.

In another aspect, a second method is provided for measuring a body impedance of a subject. The second method includes (a) propagating an alternating drive current through the subject between first and second drive current electrodes; (b) connecting a known capacitance to input nodes of a sense amplifier, the input nodes of the sense amplifier being connected to sense electrodes used to sense voltage levels of the subject resulting from the drive current; and (c) measuring a voltage differential between the input nodes of the sense amplifier while the known capacitance is connected to the input nodes of the sense amplifier. Acts (b) and (c) can be repeated a plurality of times with different values of capacitance connected to the input nodes of the sense amplifier. A body impedance value can be calculated based on the drive current and the measured voltage differentials between the input nodes of the sense amplifier for the different known capacitances connected to the input nodes of the sense amplifier. In many embodiments, acts (b) and (c) can be accomplished any suitable number of times (e.g., 1, 2, 3, 4, 5 or more) times using different values of known capacitance connected to the input nodes of the sense amplifier.

Any suitable approach can be used in the second method to calculate the body impedance value from the drive current and the measured voltage differentials. For example, an iterative approach can be used to calculate the body impedance value from the drive current and the measured voltage differentials. The second method can further include calculating impedance values for the sense electrodes including contact impedance for each of the sense electrodes.

The second method can be used in conjunction with a subject-mounted device, which may be capable of continuous subject monitoring and/or have additional functionality beyond measuring the impedance of a portion of the subject. For example, the first and second drive current electrodes and the first and second sense electrodes can be coupled to a wrist-worn device. The body impedance value calculated can include a cross-body impedance of the subject. The wrist-worn device can include an external case in contact with the user when the wrist-worn device is worn by the user. The external case can be connected to a ground. The known capacitances can be connected between at least one of the input nodes of the sense amplifier and the ground.

In another aspect, a third method is provided for measuring a body impedance of a subject. The third method includes propagating an alternating drive current through the subject between first and second drive current electrodes. A first voltage signal is generated via a first sense electrode contacted with the subject. A feedback voltage is generated in response to the first voltage signal for application to a capacitor electrically coupled to the first sense electrode to reduce the effect of a parasitic impedance on the first voltage signal of the first sense electrode. The feedback voltage is applied to the capacitor. A second voltage signal is generated via a second sense electrode contacted with the subject. A body impedance value for the subject is calculated based on the drive current and the first and second voltage signals.

In many embodiments of the third method, generating the feedback voltage includes amplifying the first voltage signal. The third method can include controlling amplification of the first voltage signal by using an automated approach so as to reduce error caused by parasitic impedance on body impedance measurement and/or controlling the amount of capacitance of the capacitor connected to the first sense electrode by using an automated approach so as to reduce error caused by parasitic impedance on body impedance measurement.

The third method can be used in conjunction with a subject-mounted device, which may be capable of continuous subject monitoring and/or have additional functionality beyond measuring the impedance of a portion of the subject. For example, the first and second drive current electrodes and the first and second sense electrodes can be coupled to a wrist-worn device. The body impedance value calculated can include a cross-body impedance of the subject. The wrist-worn device can include an external case in contact with the user when the wrist-worn device is worn by the user. The external case can be connected to a ground for the wrist-worn device.

In another aspect, a wrist-worn device is provided that can be configured to accomplish any one of the first method, second method, and third method described herein, including any described and/or suitable variation thereof. With respect to such a wrist-worn device: (a) the first drive electrode can be supported by the wrist-worn device and oriented to engage a wrist of the subject when the wrist-worn device is worn on the wrist, (b) the first sense electrode can be supported by the wrist-worn device and oriented to engage the wrist when the wrist-worn device is worn on the wrist, (c) the second drive electrode can be supported by the wrist-worn device and oriented for engagement by a first finger on an arm of the subject opposite to an arm of the subject having the wrist on which the wrist-worn device is worn, and (d) the second sense electrode can be supported by the wrist-worn device and oriented for engagement by a second finger on the arm of the subject opposite to the arm of the subject having the wrist on which the wrist-worn device is worn. At least one of the first and second drive current electrodes and/or the first and second sense electrodes can be mounted to a wrist band of the wrist-worn device.

In another aspect, a fourth method is provided for measuring a body impedance of a subject. The fourth method includes contacting a first electrode, a second electrode, a third electrode, and a fourth electrode to a subject. While maintaining contact between the subject and the first, second, third, and fourth electrodes: (a) the second, third, and fourth electrodes are connected to a ground voltage and current flowing through each of the first, second, third, and fourth electrodes resulting from application of a first known voltage to the first electrode is measured while the second, third, and fourth electrodes are connected to the ground voltage; (b) the first, third, and fourth electrodes are connected to the ground voltage and current flowing through each of the first, second, third, and fourth electrodes resulting from application of a second known voltage to the second electrode is measured while the first, third, and fourth electrodes are connected to the ground voltage; (c) the first, second, and fourth electrodes are connected to the ground voltage and current flowing through each of the first, second, third, and fourth electrodes resulting from application of a third known voltage to the third electrode is measured while the first, second, and fourth electrodes are connected to the ground voltage; and (d) the first, second, and third electrodes are connected to the ground voltage and current flowing through each of the first, second, third, and fourth electrodes resulting from application of a fourth known voltage to the fourth electrode is measured while the first, second, and third electrodes are connected to the ground voltage. A body impedance value for the subject is calculated based on the applied voltages and the measured currents.

Any suitable voltages can be used as the first, second, third, and fourth applied voltages. For example, the first, second, third, and fourth applied voltages can be substantially equal in magnitude or different in magnitude.

The fourth method can further include measuring one or more parasitic currents and using the one or more measured parasitic currents to correct measured currents used to calculate the body impedance value. For example, the fourth method can include measuring a first parasitic current with the first electrode not connected with the subject while applying the first known voltage to the first electrode. A corrected first current for the first electrode resulting from the application of the first known voltage to the first electrode can be calculated by subtracting the first parasitic current from the current measured through the first electrode while the first known voltage is applied to the first electrode and the first electrode is connected with the subject. The body impedance value can be calculated based in part on the corrected first current. The fourth method can include measuring a second parasitic current with the second electrode not connected with the subject while applying the second known voltage to the second electrode. A corrected second current for the second electrode resulting from the application of the second known voltage to the second electrode can be calculated by subtracting the second parasitic current from the current measured through the second electrode while the second known voltage is applied to the second electrode and the second electrode is connected with the subject. The body impedance value can be calculated based in part on the corrected second current. The fourth method can include measuring a third parasitic current with the third electrode not connected with the subject while applying the third known voltage to the third electrode. A corrected third current for the third electrode resulting from the application of the third known voltage to the third electrode can be calculated by subtracting the third parasitic current from the current measured through the third electrode while the third known voltage is applied to the third electrode and the third electrode is connected with the subject. The body impedance value can be calculated based in part on the corrected third current. The fourth method can include measuring a fourth parasitic current with the fourth electrode not connected with the subject while applying the fourth known voltage to the fourth electrode. A corrected fourth current for the fourth electrode resulting from the application of the fourth known voltage to the fourth electrode can be calculated by subtracting the fourth parasitic current from the current measured through the fourth electrode while the fourth known voltage is applied to the fourth electrode and the fourth electrode is connected with the subject. The body impedance value can be calculated based in part on the corrected fourth current.

In another aspect, a wrist-worn device is provided that can be configured to accomplish the fourth method, including any described and/or suitable variation thereof. With respect to such a wrist-worn device: (a) the first electrode can be supported by the wrist-worn device and oriented to engage a wrist of the subject when the wrist-worn device is worn on the wrist, (b) the second electrode can be supported by the wrist-worn device and oriented to engage the wrist when the wrist-worn device is worn on the wrist, (c) the third electrode can be supported by the wrist-worn device and oriented for engagement by a first finger on an arm of the subject opposite to an arm of the subject having the wrist on which the wrist-worn device is worn, and (d) the fourth electrode can be supported by the wrist-worn device and oriented for engagement by a second finger on the arm of the subject opposite to the arm of the subject having the wrist on which the wrist-worn device is worn. At least one of the first electrode, the second electrode, the third electrode, and the fourth electrode can be mounted to a wrist band of the wrist-worn device.

In another aspect, a wrist-worn device for measuring a body impedance of a user is provided. The wrist worn device includes, a housing, a first electrode, a second electrode, a third electrode, a fourth electrode, and a control unit. The housing is configured to be worn on a user's wrist. The first electrode is coupled with the housing and oriented to engage the user's wrist when the wrist-worn device is worn on the user's wrist. The second electrode is coupled with the housing and oriented to engage the user's wrist when the wrist-worn device is worn on the user's wrist. The third electrode is coupled with the housing and oriented for engagement by a first finger on an arm of the user opposite to an arm of the user having the wrist on which the wrist-worn device is worn. The fourth electrode is coupled with the housing and oriented for engagement by a second finger on the arm of the user opposite to the arm of the user having the wrist on which the wrist-worn device is worn. The control unit is operatively coupled with the first, second, third, and fourth electrodes. The control unit is configured to measure a body impedance of the user via the first, second, third, and fourth electrodes. The control unit employs a means for reducing parasitic effects in the measurement of the body impedance of the user.

The preceding presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
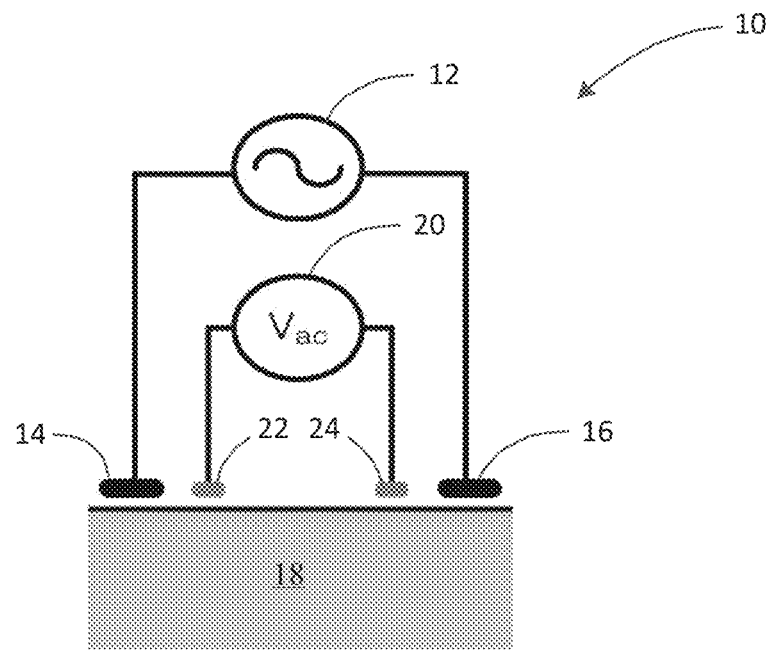
FIG. 1 schematically illustrates a four-electrode configuration used to measure impedance of a subject, in accordance with many embodiments.

Referring now to the drawings, in which like reference numerals represent like parts throughout the several views, FIG. 1 schematically illustrates a tetra-polar electrode configuration 10 used to measure impedance of a subject, in accordance with many embodiments. The tetra-polar electrode configuration 10 includes a drive current generator 12 electrically coupled with a first drive current electrode 14 and a second drive current electrode 16. In many embodiments, the drive current generator 12 imparts an alternating current to a subject 18 via the electrodes 14, 16. The tetra-polar electrode configuration 10 also includes a voltage sensor 20 electrically coupled to the subject 18 via a first sense electrode 22 and a second sense electrode 24. The use of the sense electrodes 22, 24, which are separated from the drive current electrodes 14, 16, serves to reduce the impact of impedance and contact resistance by sensing voltage with electrodes that are transferring much lower levels of current relative to the current drive electrodes 14, 16. In many embodiments, the applied alternating drive current preferably has a frequency between 20 kHz and 100 kHz. In some of these embodiments, a drive current of about 85 kHz is preferred.

Figure 2:
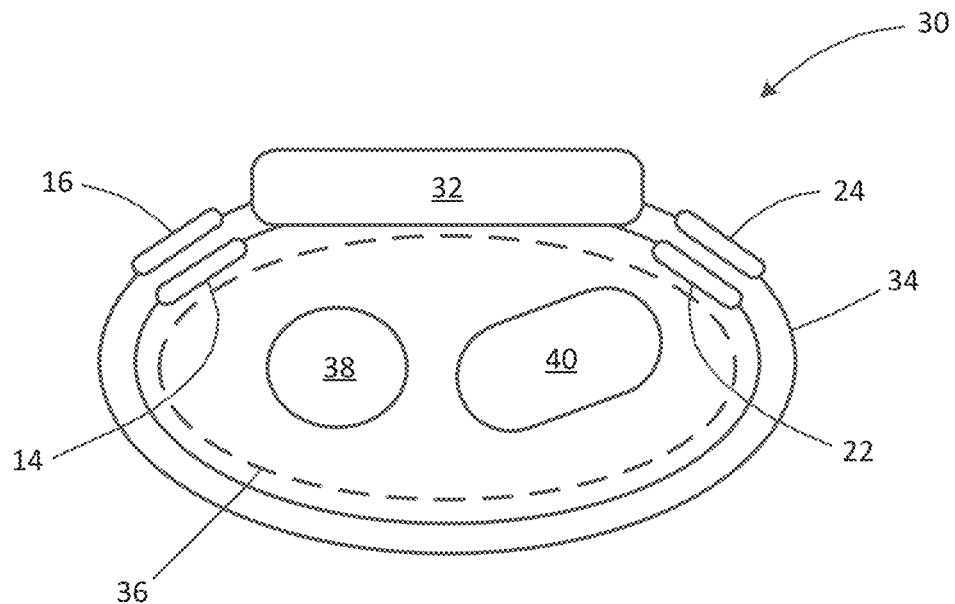
FIG. 2 is a schematic side view of a wrist-worn device configured to measure the impedance of a subject, in accordance with many embodiments.

FIG. 2 shows a side view of a wrist-worn impedance measurement device 30, in accordance with many embodiments. The wrist-worn device 30 includes a main unit 32, a wrist-worn elongate band 34, a first drive current electrode 14, a first sense electrode 22, a second drive current electrode 16, and a second sense electrode 24. The first drive current electrode 14 and the first sense electrode 22 are: 1) supported on the wrist-worn elongate band 34, 2) positioned and oriented to interface with a subject's wrist upon which the wrist-worn device 30 is worn, and 3) operatively connected with the main unit 32. The second drive current electrode 16 and the second sense electrode 24 are: 1) supported on the wrist-worn elongate band 34, 2) positioned and oriented to be interfaceable with the subject so that the drive current travels through the thoracic cavity of the subject (e.g., with separate fingers on the arm opposite to the arm on which the wrist-worn device 30 is worn), and 3) operatively connected with the main unit 32. The main unit 32 includes circuitry and/or software for imparting drive current through the subject via the first and second drive current electrodes 14, 16 and for processing signals from the first and second sense electrodes 22, 24 so as to measure a body impedance of the subject wearing the wrist-worn device 30.

The wrist-worn device 30 has the first drive current electrode 14 and the first sense electrode 22 located to enhance contact pressure with a wrist 36 of the subject. In the illustrated embodiment, the first drive current electrode 14 is disposed on an opposite inside surface of the wrist-worn band 34 relative to the second drive current electrode 16 such that contact pressure between, for example, a finger of the subject and the second drive current electrode 16 transfers compression through the wrist-worn band 34 to the first drive current electrode 14, thereby increasing contact pressure between the first drive current electrode 14 and the wrist 36. In a similar fashion, the first sense electrode 22 is disposed on an opposite inside surface of the wrist-worn band 34 relative to the second sense electrode 24 such that contact pressure between, for example, a finger of the subject and the second sense electrode 24 transfers compression through the wrist-worn band 34 to the first sense electrode 22, thereby increasing contact pressure between the first sense electrode 22 and the wrist 36. Any suitable variation can be used. For example, the locations of the first drive current electrode 14 and the first sense electrode 22 can be exchanged. As another example, the electrodes 14, 16, 22, 24 can be located at any other suitable locations on the wrist-worn band 34. As another example, any suitable number of the electrodes 14, 16, 22, 24 can be disposed on the main unit 32. Cross sections of the ulna bone 38 and the radius bone 40 of the subject are shown for reference.

Figure 3:
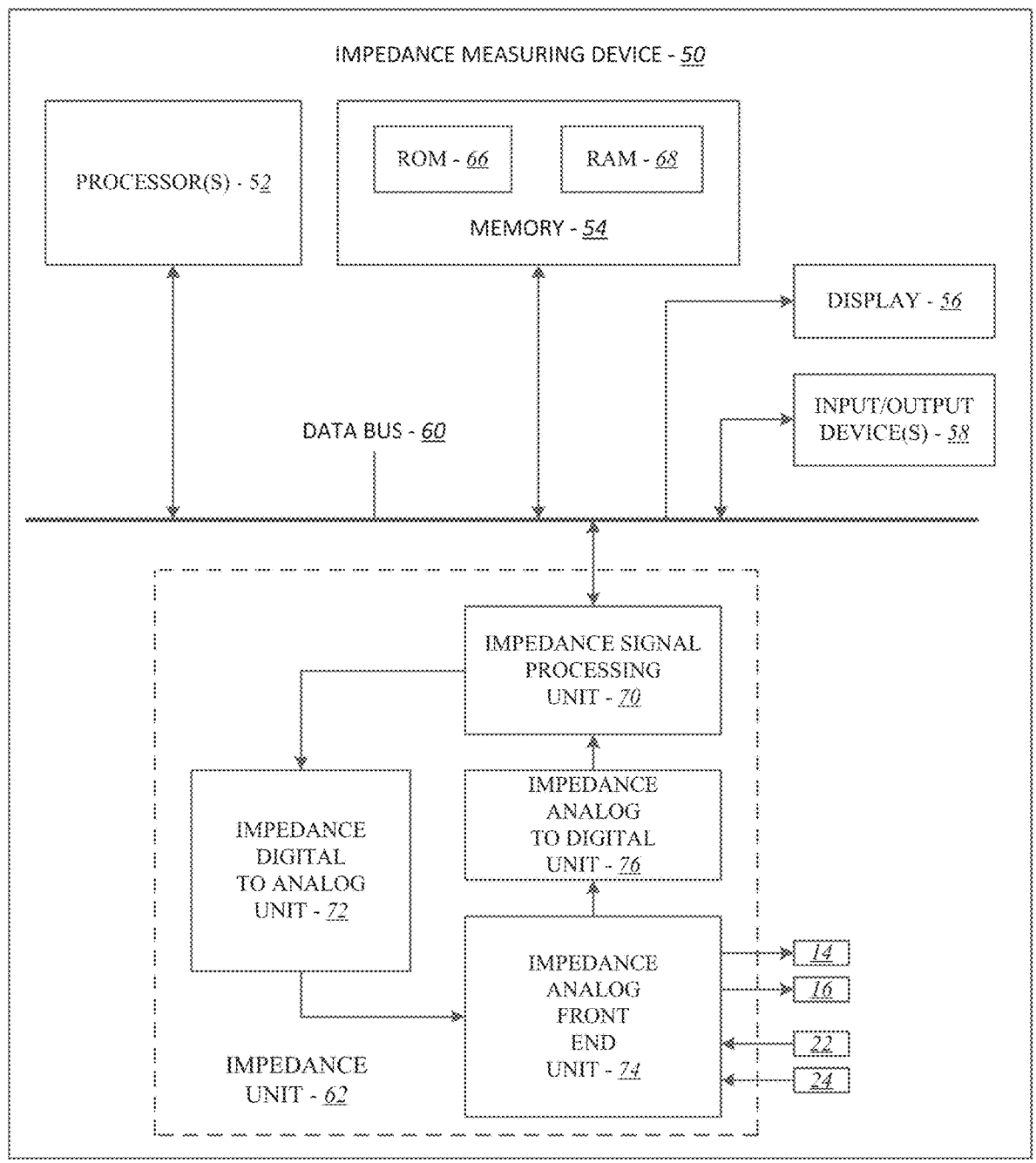
FIG. 3 is a schematic diagram of a device configured to measure impedance of a subject, in accordance with many embodiments.

FIG. 3 schematically represents an embodiment of a device 50 for measuring an impedance of a subject. In the illustrated embodiment, the device 50 includes one or more processors 52, memory 54, a display 56, one or more input/output devices 58, a data bus 60, and an impedance unit 62. In many embodiments, the memory 54 includes read only memory (ROM) 66, and random access memory (RAM) 68. The one or more processors 52 can be implemented in any suitable form, including one or more field-programmable gate arrays (FPGA).

The impedance unit 62 can have any suitable configuration to generate the alternating drive current applied to the subject via the first and second drive current electrodes 14, 16 for propagation through the subject and process the resulting subject voltages sensed by the sense electrodes 22, 24 to determine one or more impedance values for the subject. For example, in the illustrated embodiments, the impedance unit 62 includes an impedance signal processing unit 70, an impedance digital to analog unit 72, an impedance analog front end unit 74, and an impedance analog to digital unit 76. The signal processing unit 70 generates a digital alternating drive signal (e.g., a digital drive signal corresponding to an 85 kHz sinusoidal drive current) and supplies the digital alternating drive signal to the digital to analog unit 72. The digital to analog unit 72 generates a sinusoidal drive current matching the digital alternating drive signal and supplies the sinusoidal drive current to the analog front end unit 74. The analog front end unit 74 supplies the sinusoidal drive current to the first and second drive current electrodes 14, 16 for propagation through the subject. Resulting voltage levels are sensed via the first and second sense electrodes 22, 24. Signals from the sense electrodes 22, 24 are processed by the analog front end 74 to generate an analog voltage signal supplied to the analog to digital unit 76. The analog to digital unit 76 converts analog voltage signal to a corresponding digital signal that is supplied to the signal processing unit 70. The signal processing unit 70 then generates corresponding impedance digital data that can be processed by the one or more processors 52 to determine one or more impedance values for the subject using any suitable approach, including the approaches described herein.

Figure 4:
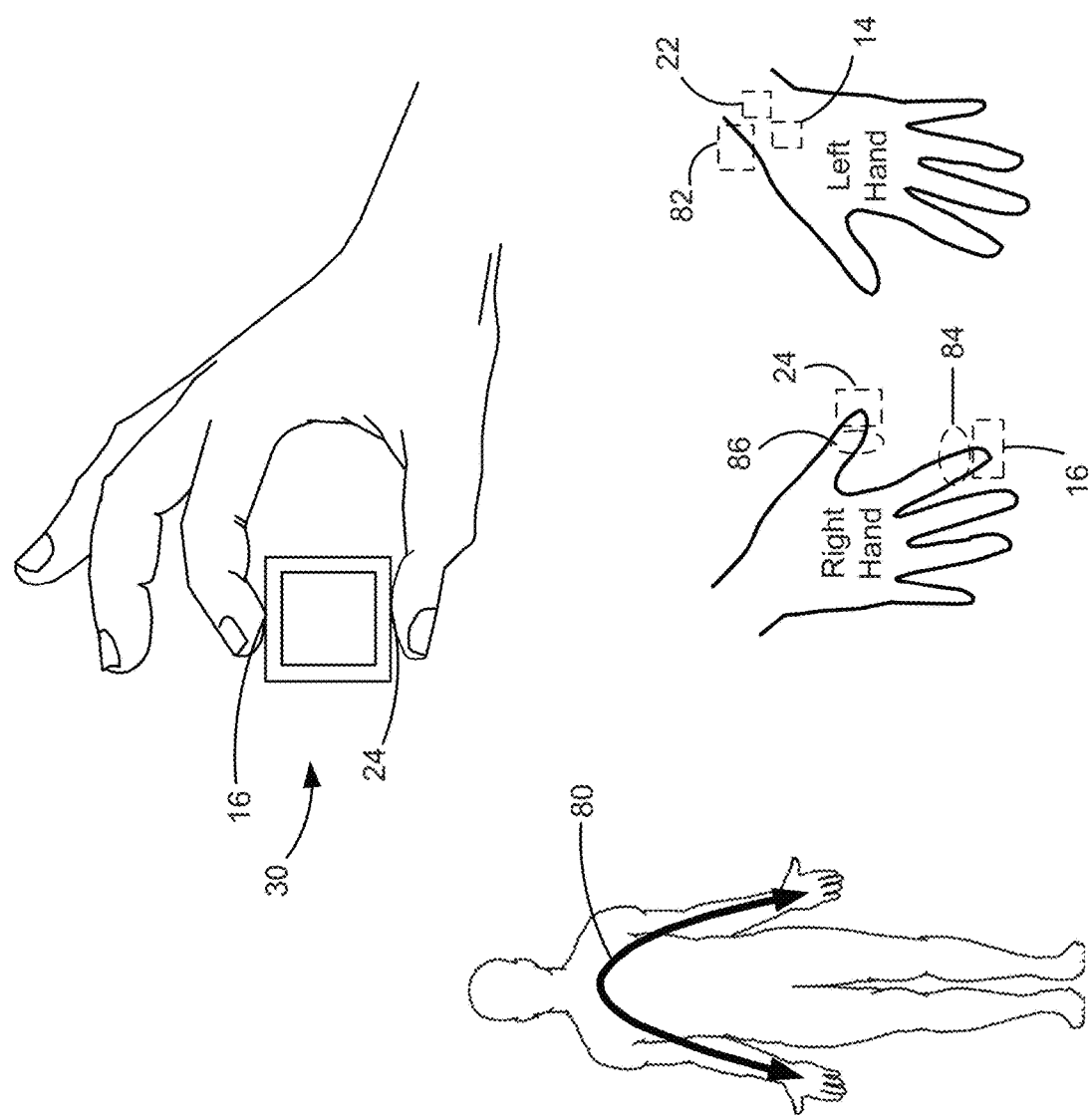
FIG. 4 schematically illustrates electrode locations in an approach for measuring impedance of a subject, in accordance with many embodiments.
Figure 5:
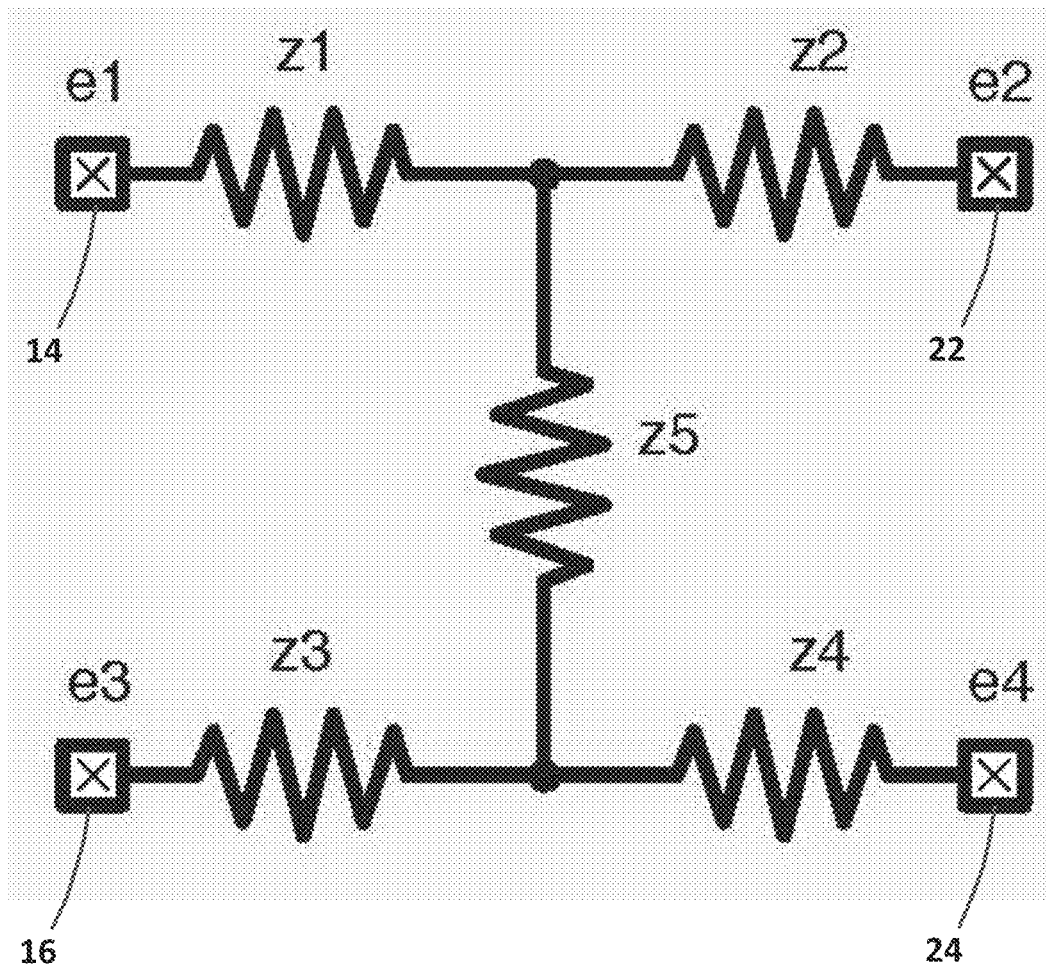
FIG. 5 schematically illustrates electrode impedances and a body impedance in an approach for measuring impedance of a subject, in accordance with many embodiments.

FIGS. 4 and 5 schematically illustrate electrode locations, electrode impedances, and a body impedance in an approach for measuring impedance of a subject, in accordance with many embodiments. In the illustrated approach, the first drive current electrode 14 and the first sense electrode 22 are held in contact with the left wrist of the subject. The second drive current electrode 16 is contacted by the right index finger of the subject. The second sense electrode 24 is contacted by the right thumb of the subject. The first and second drive current electrodes 14, 16 impart a cross-body alternating drive current 80 between the drive current electrodes 14, 16. The cross-body drive current 80 propagates through the left wrist, through the left arm, through the thoracic cavity, through the right arm, and through the right index finger. The combined impedance of the left wrist local to the first drive current electrode 14 and the contact impedance of the first drive current electrode 14 and the left wrist is schematically represented as an impedance (z1). The combined impedance of the right index finger in contact with the second drive current electrode 16 and the contact impedance of the second drive current electrode 16 and the right index finger is schematically represented as an impedance (z3). The net cross-body impedance between the impedances (z1 and z3) is schematically represented as an impedance (z5). The combined impedance of the left wrist local to the first sense electrode 22 and the contact impedance of the first sense electrode 22 and the left wrist is schematically represented as an impedance (z2). The combined impedance of the right thumb in contact with the second sense electrode 24 and the contact impedance of the second sense electrode 24 and the right thumb is schematically represented as an impedance (z4). In many embodiments, because the first and second sense electrodes 22, 24 are configured to measure a voltage differential without transferring any significant amount of current, the resulting voltage drops across the impedances (z2 and z4) are small so that the voltage differential sensed by the first and second sense electrodes 22, 24 may better match the voltage differential across the impedance (z5).

Figure 6:
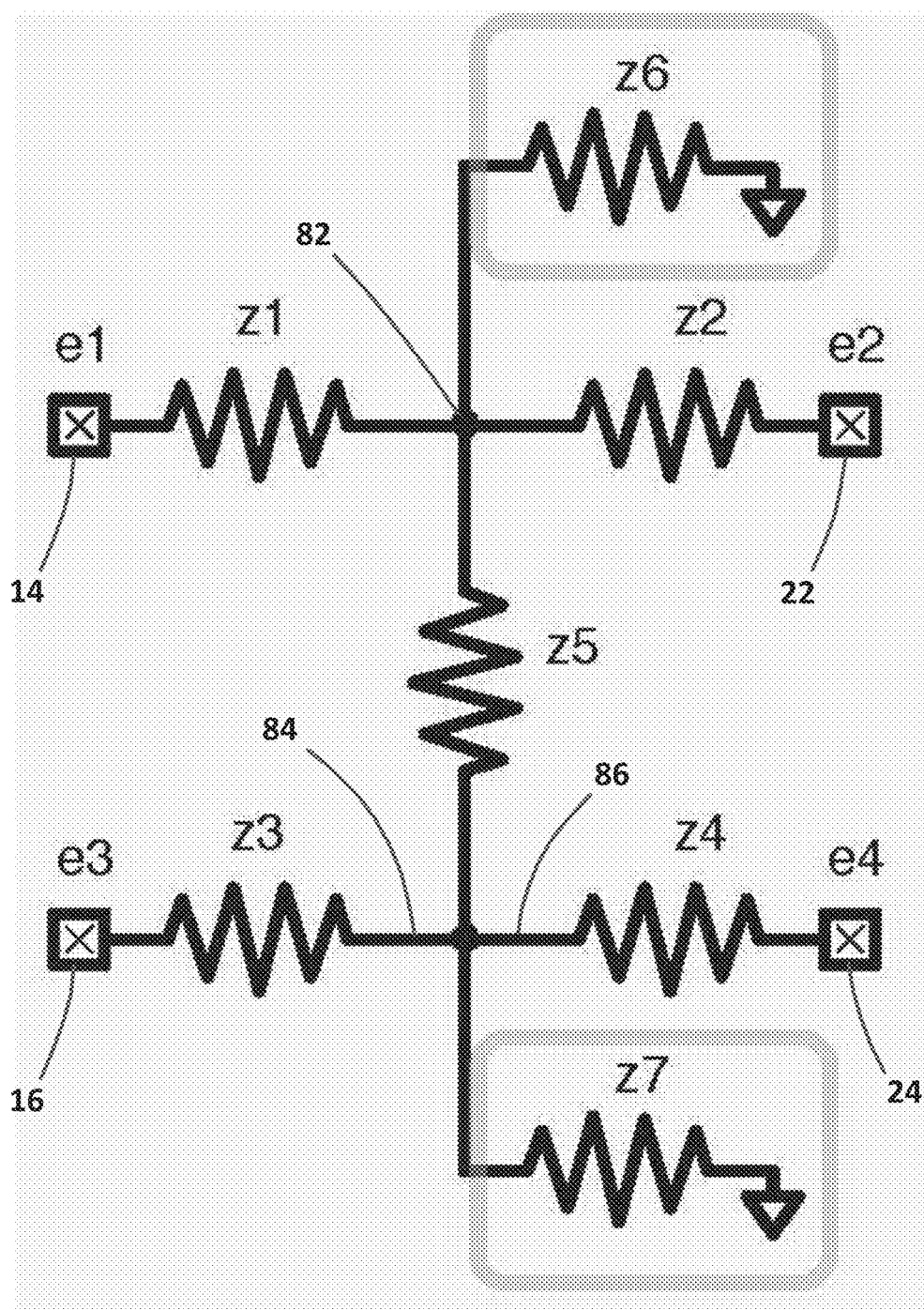
FIG. 6 schematically illustrates electrode impedances, a body impedance, and parasitic current paths through device chassis impedances in an approach for measuring impedance of a subject with a subject-mounted device, in accordance with many embodiments.

FIG. 6 is a simplified schematic circuit diagram illustrating a tetra-polar electrode impedance measurement having parasitic currents arising due to contact between the subject and the chassis of a device used to perform the impedance measurement. In an example configuration, the impedance measurement device is a wrist-worn device having a chassis that serves as an electrical ground for the device. To prevent the occurrence of a voltage differential between the subject and the chassis, the chassis can be conductive and contacted with the subject. With such a chassis serving as an electrical ground, the applied current through the first and second drive electrodes 14, 16 can result in a voltage level within the subject at a location contacted with the chassis that differs from the voltage level of the chassis. For example, referring to FIG. 4, the chassis of the wrist-worn device can contact the subject's left wrist at a wrist location 82. Due to the drive current introduced via the drive electrodes 14, 16, the voltage at the wrist location 82 can differ from the ground voltage of the chassis, thereby generating an associated parasitic current between the wrist location 82 and the chassis of the wrist-worn device. The path for this parasitic current between the wrist location 82 of the subject and the chassis of the wrist-worn device is represented as an impedance (z6) in FIG. 6. In a similar fashion, referring again to FIG. 4, the chassis of the wrist-worn device can be contacted by the subject's right index finger at an index finger location 84 and/or the chassis of the wrist-worn device can be contacted by the subject's right thumb at a thumb location 86. Again, due to the drive current introduced via the drive electrodes 14, 16, the voltage at the index finger location 84 can differ from the ground voltage of the chassis, thereby generating an associated parasitic current between the index finger location 84 and the chassis of the wrist-worn device. Likewise, the voltage of the thumb location 86 can differ from the ground voltage of the chassis, thereby generating an associated parasitic current between the thumb location 86 and the chassis of the wrist-worn device. The path for this parasitic current between the index finger location 84 and/or the thumb location 86 of the subject and the chassis of the wrist-worn device is represented as an impedance (z7) in FIG. 6. The parasitic currents between the subject and the chassis through the impedances (z6 and/or z7) can introduce error into the impedance measurement by causing the current that flows through the body portion being measured (represented by z5) to differ from the current applied via the drive current electrodes 14, 16.

Figure 7:
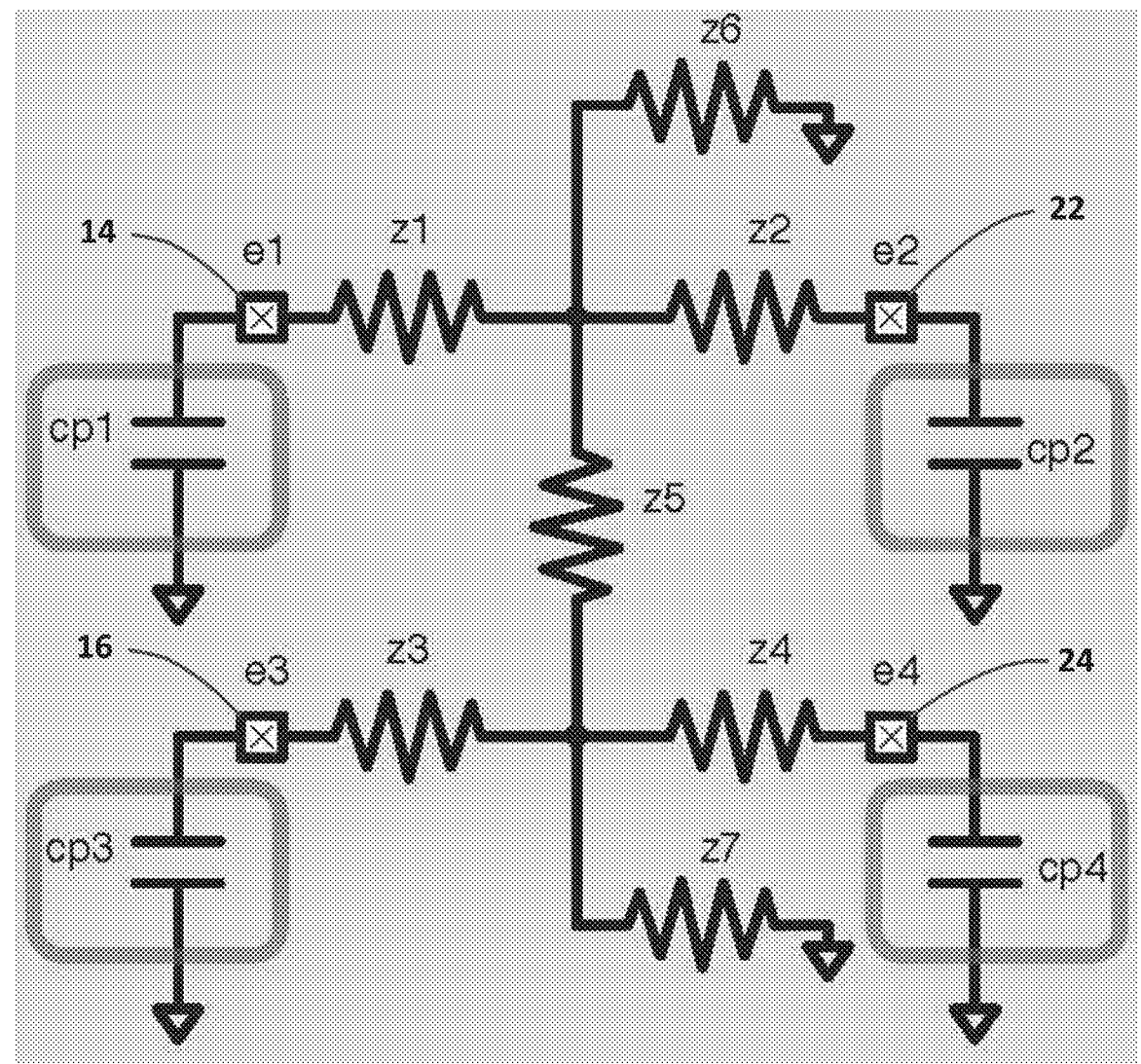
FIG. 7 schematically illustrates electrode impedances, a body impedances, parasitic current paths, and parasitic current paths through device chassis impedances in an approach for measuring impedance of a subject with a subject-mounted device, in accordance with many embodiments.

In addition to the impedance measurement error that can result due to chassis contact related parasitic current(s), impedance measurement error can result due to parasitic capacitances inherent in the impedance measurement device, such as the parasitic capacitances (cp1, cp2, cp3, and cp4) schematically represented in FIG. 7. For example, parasitic capacitances (cp1 and cp3) can be associated with the drive current generator 12 used to apply the current to the subject via the first and second drive current electrodes 14 and 16. Parasitic capacitances (cp2 and cp4) can be associated with the voltage sensor 20 used to sense the resulting voltage differential in the subject at the location contacted by the first and second sense electrodes 22, 24.

The impedance measurement methods and devices described herein can be used in conjunction with coated metal electrodes. The use of coated metal electrodes avoids the use of gel-based electrodes, which are limited with respect to the number of times that they can be used. The electrode impedances can vary depending on the electrode material used and can be as much as 10 to 100 times the body impedance.

Figure 8:
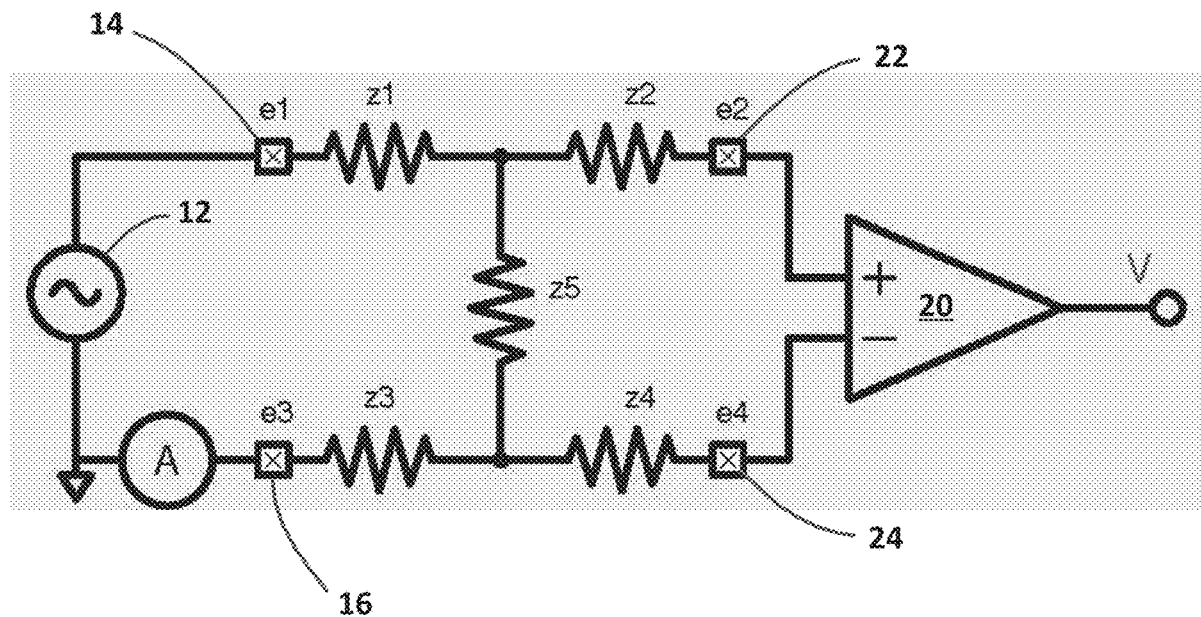
FIG. 8 schematically illustrates a basic tetra-polar electrode approach for measuring body impedance.
Figure 9:
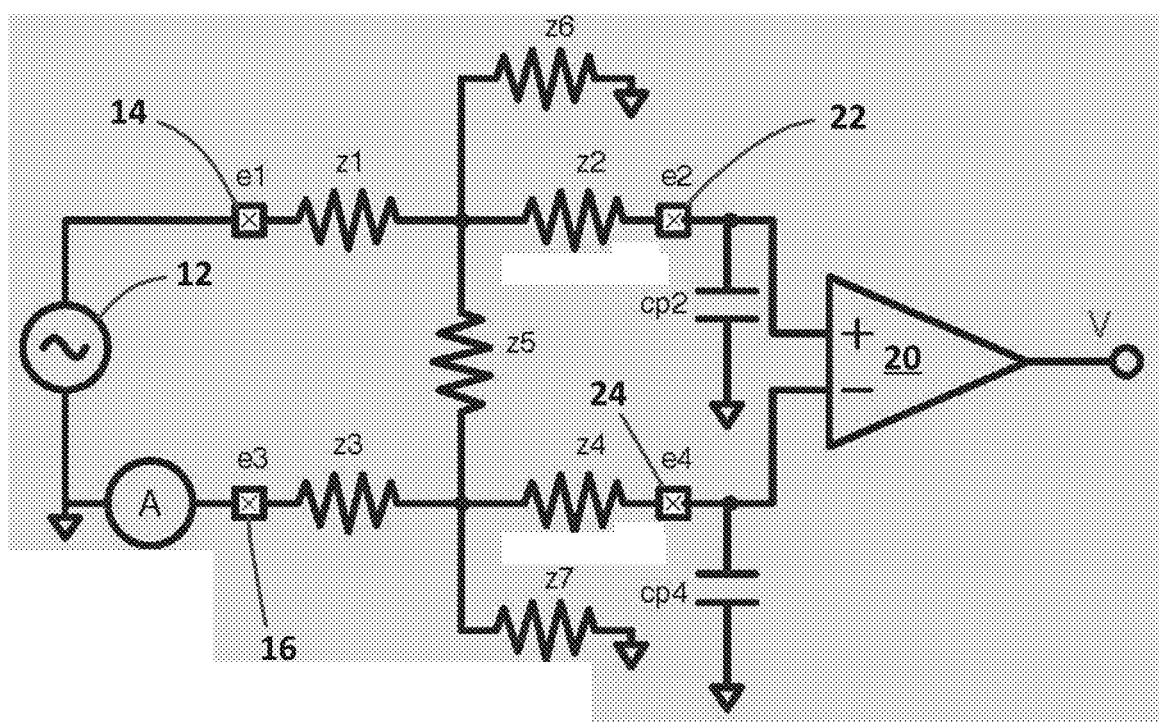
FIGS. 9 and 10 schematically illustrates a parasitic current that induces error in a tetra-polar electrode approach for measuring body impedance.
Figure 10:
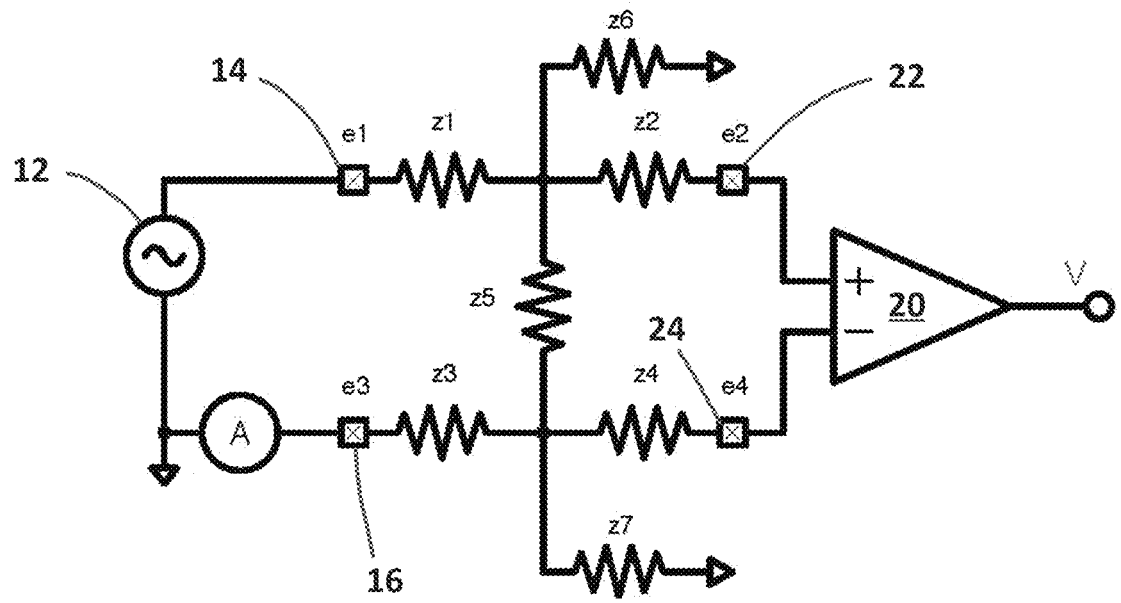

FIG. 8 schematically illustrates idealized assumptions made with respect to the tetra-polar electrode approach for measuring body impedance (referred to herein as the basic tetra-polar system). Such idealized assumptions fail to account for parasitic currents that may arise due to the presence of parasitic capacitances and/or parasitic system couplings as described herein. For example, in the absence of significant parasitic currents, it is assumed that the current through the body impedance (z5) being measured equals the current applied by the drive current generator 12. And in the absence of significant current flowing through the sense electrodes (impedances z2 and z3), the voltage differential measured by the voltage sensor 20 via the sense electrodes 22, 24 is assumed to be the voltage differential across the impedance (z5) being measured. Such assumptions, however, may not be valid where significant parasitic currents exist, such as described herein. For example, where significant parasitic currents exist such as illustrated in FIGS. 9 and 10, the current flowing through the impedance (z5) being measured is not equal to the current applied by the drive current generator 12. Additionally, due to parasitic current flowing through the sense electrodes (impedances z2 and z3) as a result of the existence of the parasitic capacitances (cp2 and cp4), the voltage differential measured by the voltage sensor 20 via the sense electrodes 22, 24 is not equal to the voltage differential across the impedance (z5) being measured. As a result, the impedance being measured is not given by dividing the voltage sensed by the voltage sensor 20 by the current applied by the drive current generator 12. While such measurement devices can be quite sophisticated (optionally including additional components, systems, capabilities and the like), they are sometimes referred to herein as basic tetra-polar electrode systems.

Virtual Ground

Figure 11:
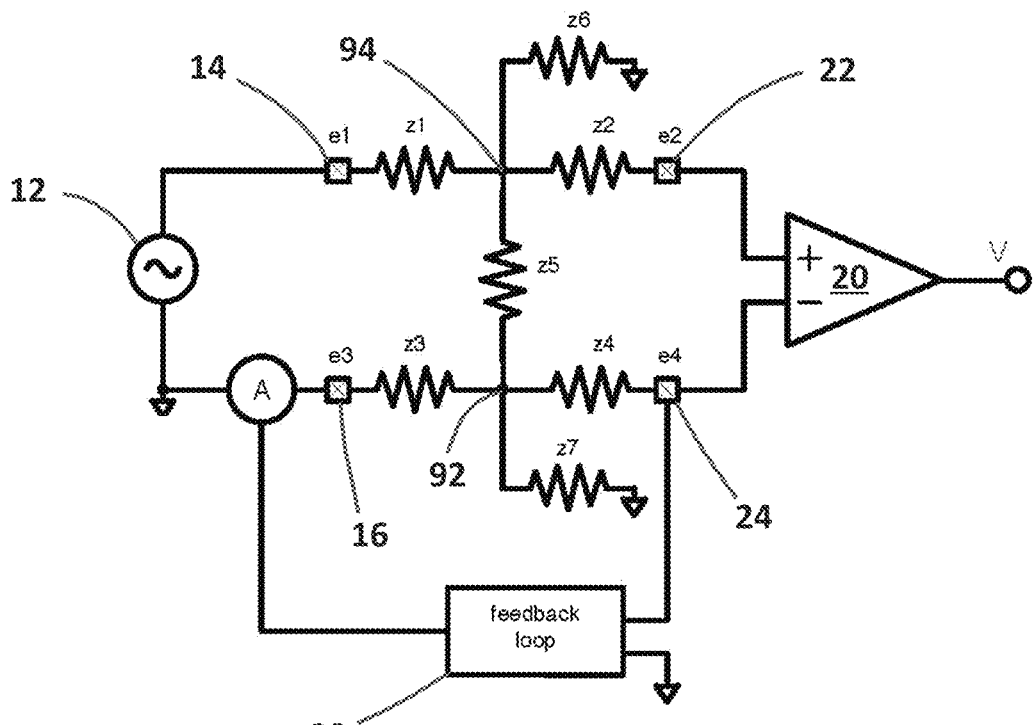
FIGS. 11 and 12 schematically illustrate the use of feedback loops to reduce a parasitic current that induces error in a tetra-polar electrode approach for measuring body impedance, in accordance with many embodiments.

FIG. 11 schematically illustrates the use of a feedback loop 90 that is configured to control the voltage level of a sense electrode to reduce current flowing through the impedance (z7), which represents a current path arising from contact with the chassis of the impedance measurement device, thereby reducing measurement error induced via current flow through the impedance (z7). In the illustrated embodiment, the feedback loop 90 is connected between the second drive current electrode 16 and the second sense electrode 24. The combination of the drive current generator 12 and the feedback loop 90 applies a current via the drive current electrodes 14, 16 such that the voltage level of the second sense electrode 24 is maintained substantially equal to the reference ground voltage. With the voltage of the second sense electrode being maintained substantially equal to the reference ground voltage, the voltage of node 92 (which has the same or close to the same voltage level of the second sense electrode 24) is likewise maintained to be substantially equal to the reference ground voltage thereby maintaining a substantially zero voltage potential across the impedance (z7) so that substantially no current flows through the impedance (z7). Alternatively, a feedback loop can be connected between the first drive current electrode 14 and the first sense electrode 22 so as to maintain the voltage of the first sense electrode 22 (and hence the voltage of a node 94) substantially equal to the reference ground voltage, thereby resulting in substantially zero parasitic current flow through the impedance (z6), which represents another current path arising from contact between the subject and the chassis of the impedance measurement device.

Figure 12:
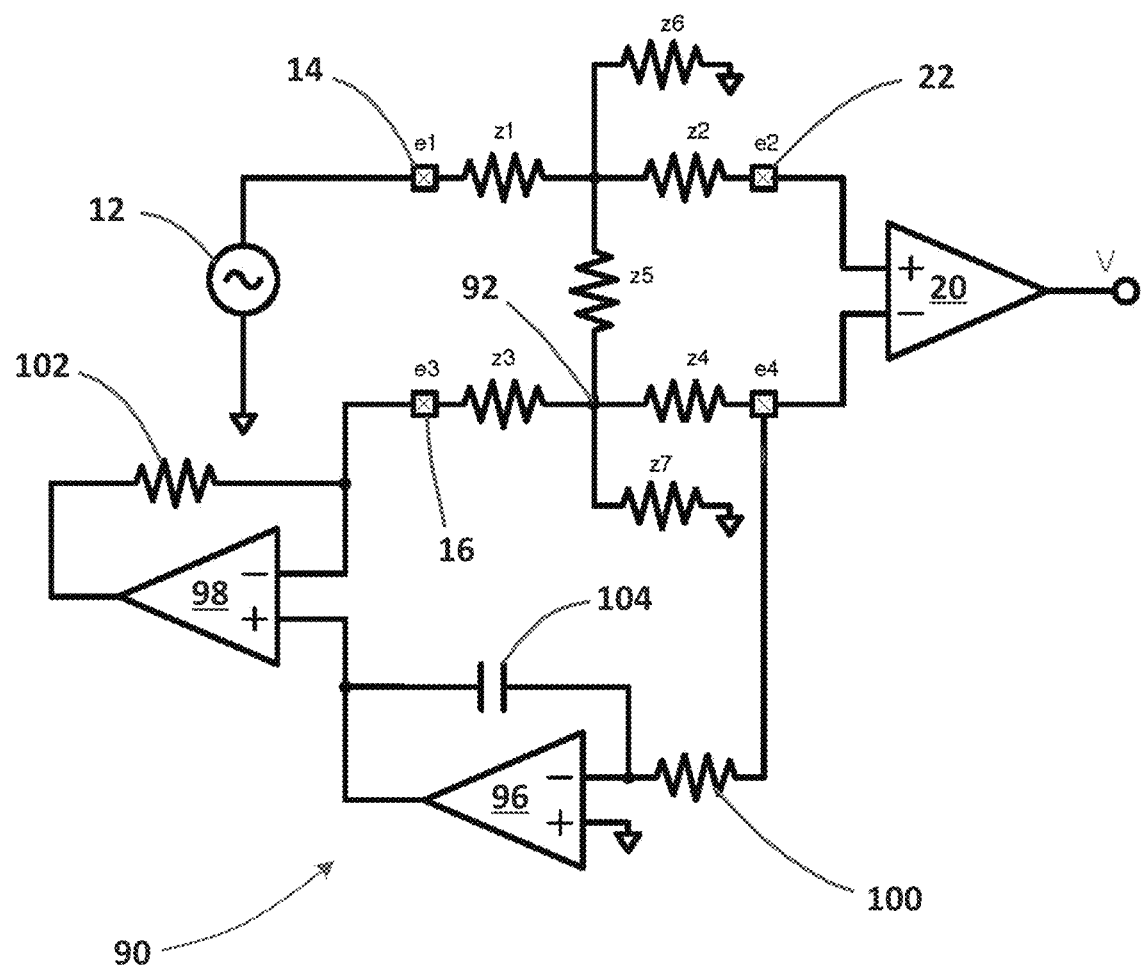

FIG. 12 schematically illustrates an embodiment of the feedback loop 90. The illustrated embodiment of the feedback loop 90 includes an integrator 96, a trans impedance amplifier (TIA) 98, a first resistor 100, a second resistor 102, and a capacitor 104. In the illustrated embodiment, the first resistor 100 is connected between the second sense electrode 24 and a negative input of the integrator 96. A positive input of the integrator 96 is connected to ground. The output of the integrator 96 is connected to a positive input of the TIA 98. The capacitor 104 is connected between the negative input of the integrator 96 and the positive input of the TIA 98. The second drive current electrode 16 is connected to a negative input of the TIA 98. The second resistor 102 is connected between the output of the TIA 98 and the negative input of the TIA 98. The drive current generator 12 is connected to the first drive current electrode 14 and disconnected from the second drive current electrode 16.

The integrator 96 is used to implement the feedback that maintains the voltage of node 92 to be substantially equal to the reference ground voltage. When the voltage of the second sense electrode 24 is higher than the reference ground voltage, the integrator 96 outputs a voltage lower than the reference ground voltage. The TIA 98 has a non-inverting input that sets the voltage of the second drive current electrode 16. Accordingly, the integrator output sets the voltage of the second drive current electrode 16 such that the voltage of the second sense electrode 24 is equal to the reference ground voltage. Assuming that the IR drop across impedance (z4) is negligible, the feedback loop 90 sets the internal node 92 to the reference ground voltage. If, however, the IR drop across the impedance (z4) is non-negligible, the voltage of the internal node 92 may deviate somewhat from the reference ground voltage. Even if the voltage of the internal node 92 deviates somewhat from the reference ground voltage, the feedback loop 90 may still substantially reduce the parasitic current flowing through the chassis contact related impedance (z7).

Capacitance Addition

Figure 13:
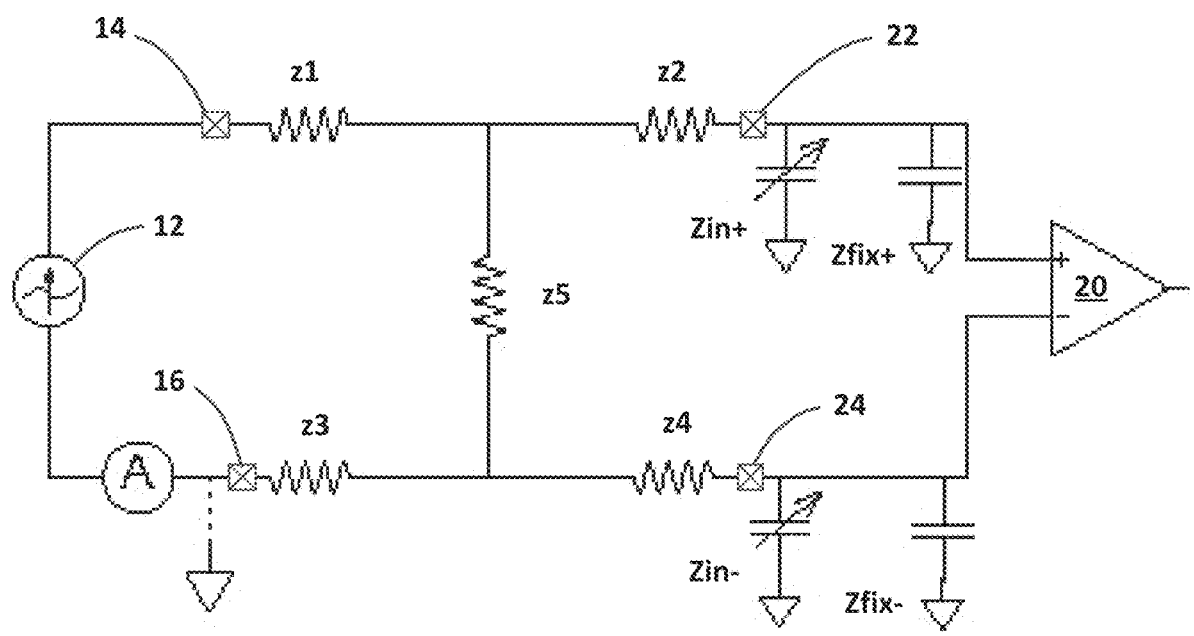
FIG. 13 schematically illustrates an approach for measuring a body impedance in which known capacitances are added to enable determination of unknown electrode impedances, in accordance with many embodiments.

FIG. 13 schematically illustrates an approach for measuring body impedance (z5) that iteratively adds different known capacitances to the input nodes of the voltage sensor 20. For each of the added capacitances, measurements for Vo+, Vo−, and Idrive are obtained. For example, measurements for Vo+, Vo−, and Idrive can be obtained for each of a suitable number (e.g., 5) different capacitances (Zin+, Zin−) added to the input nodes of the voltage sensor 20 as illustrated. The different sets of measured voltages and current can be used to solve for the three unknown impedances (i.e., body impedance (z5), first sense electrode impedance (z2), and second sense electrode impedance (z4)). The voltage sensor first input impedance (Zfix+) and the voltage sensor second input impedance (Zfix−) are known constants.

In the absence of the sense electrode impedances (z2, z4) and the voltage sensor parasitic input impedances (Zfix+, Zfix−), the body impedance (z5) would be given by equation (1).

$$Z_{5,meas} = (V_o^+ + V_o^-)/I_{drive} \qquad \text{equation (1)}$$

Given the existence of the parasitic input impedances (Zfix+, Zfix−) and the sense electrode impedances (z2, z4), equation (2) can be used to determine the body impedance (z5), as well as the sense electrode impedances (z2, z4).

$$Z_{5,calc} = \frac{Z_5 Z'_{in+} Z'_{in-} (V_o^+ V_o^-)}{(V_o^+ V_o^-) Z'_{in+} Z'_{in-} + (Z'_{in-} Z_2 V_o^+ - Z'_{in+} Z_4 V_o^-)} \qquad \text{equation (2)}$$

$$\text{where: } Z'_{in-} = \frac{Z_{in-} Z_{fix-}}{Z_{in-} + Z_{fix-}} \qquad \text{equation (3)}$$

$$\text{where: } Z'_{in+} = \frac{Z_{in+} Z_{fix+}}{Z_{in+} + Z_{fix+}} \qquad \text{equation (4)}$$

For each added capacitance, the measurements for Vo+, Vo−, and Idrive, the added capacitances (Zin+, Zin−), estimated values of the body impedance (z5) and the sense electrode impedances (z2, z4), and equation (2) are used to calculate a corresponding $Z_{5,calc}$. The estimates for the body impedance (z5) and the sense electrode impedances (z2, z4) can then be refined based on differences between $Z_{5,meas}$ as given by equation (1) and $Z_{5,calc}$ as given by equation (2) until there is negligible error between the two values. The initial estimates for the impedances of the sense electrodes (z2, z4) can be based on previously determined values for these impedances.

The number of different capacitances added is primarily used to determine the impedances of the sense electrodes (z2, z4). For example, where the impedance of the sense electrodes (z2, z4) is known, a single set of measurements of Vo+, Vo−, and Idrive can be used to determine the corresponding body impedance (z5). Where the impedance of the sense electrodes (z2, z4) is not known, if the estimated values of the impedances of the sense electrodes differs significantly from the actual values, no single estimated value of the body impedance can be selected for which $Z_{5,calc}$ equals $Z_{5,meas}$ for each of the measurements sets for the respective added capacitances. Therefore, the estimated values of the impedances of the sense electrodes (z2, z4) can be adjusted to achieve negligible difference between $Z_{5,calc}$ and $Z_{5,meas}$ for each of the measurements sets for the respective added capacitances.

Capacitance Subtraction

Figure 14:
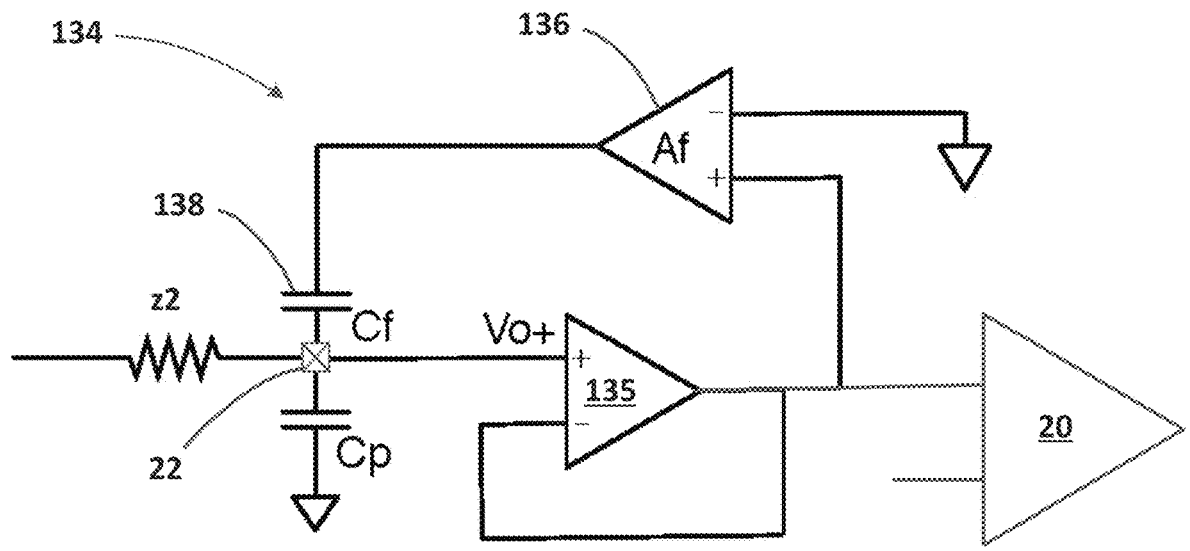
FIG. 14 schematically illustrates an approach for measuring a body impedance in which a feedback voltage is applied to a capacitor connected to sense electrode to reduce impedance measurement error, in accordance with many embodiments.

FIG. 14 schematically illustrates the use of a positive feedback loop 134 to reduce the parasitic capacitance (Cp) of the sense electrode 22 to Cp−(Af−1)Cf. The positive feedback loop 134 is connected between the sense electrode 22 and the voltage sensor 20. The positive feedback loop 134 includes a capacitor 138 connected to the sense electrode 22. The positive feedback loop applies a feedback voltage to the capacitor 138, thereby affecting the voltage of the sense electrode 22. The positive feedback loop 134 increases the impedance (Zin given in equation (5)) looking into the voltage sensor 20 thereby reducing the error caused by the parasitic impedance (Cp) on the body impedance measurement.

$$Z_{in} = \frac{1}{(C_p - (A_f - 1)C_f)s} \qquad \text{equation (5)}$$

In the feedback loop 134, the sense electrode 22 is connected to the positive input of a first voltage amplifier 135 and the output of the first voltage amplifier is connected to the positive input of the first voltage amplifier 135. The output of the first voltage amplifier 135 is connected to the positive input of a second voltage amplifier 136. The negative input of the second voltage amplifier is connected to ground. The output of the second voltage amplifier is applied to one side of the capacitor 138 and the other side of the capacitor 138 is connected to the sense electrode 22. The amplification factor (Af) of the second amplifier 136 and/or the capacitance of the capacitor 138 can be controlled using an automated approach so as to reduce error caused by parasitic impedance on body impedance measurement. For example, for automated control of the capacitance, a bank of capacitors can be used in the feedback. The capacitors can be added until the loop becomes unstable. At this point the loop is overcompensated. Accordingly, a few capacitors from the bank can be removed and the remaining capacitance used to compensate the parasitic capacitance. Any suitable variation of the feedback loop 134 can be used. For example, the second amplifier 136 can be omitted and the voltage output by the first voltage amplifier 135 fed directly to the capacitor 138.

The feedback loop 134 can be used in a subject-mounted device for measuring a body impedance of the subject. Such a subject-mounted device can be capable of continuous subject monitoring and/or have additional functionality beyond measuring the impedance of a portion of the subject. For example, the first and second drive current electrodes and the first and second sense electrodes can be coupled to a wrist-worn device. The body impedance value calculated can include a cross-body impedance of the subject. The wrist-worn device can include an external case in contact with the user when the wrist-worn device is worn by the user. The external case can be connected to a ground voltage for the wrist-worn device.

Admittance Matrix

Figure 15:
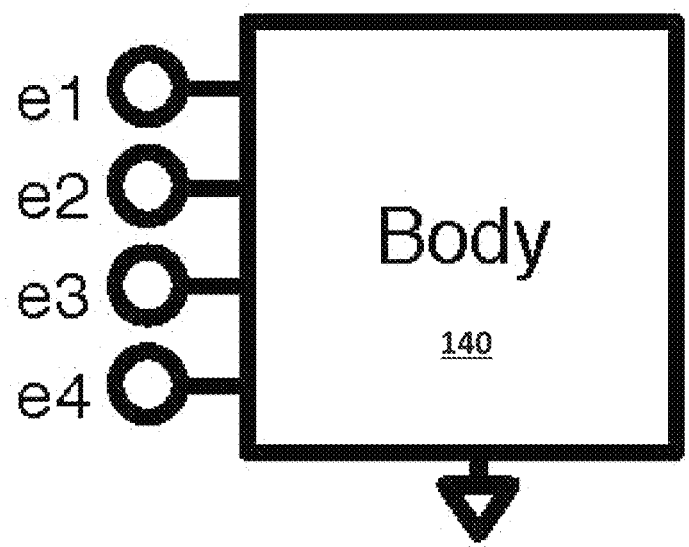
FIG. 15 schematically illustrates connections to a body for measuring impedance of the body using an indefinite admittance matrix approach, in accordance with many embodiments.

FIG. 15 schematically illustrates connections (electrodes e1, e2, e3, e4) to a subject 140 for measuring impedance of the subject 140 using an indefinite admittance matrix approach. In the indefinite admittance matrix approach, the electrodes (e1, e2, e3, e4) are interfaced with the subject 140. The electrodes (e1, e2, e3, e4) are interfaced with the subject 140.

Figure 16A:
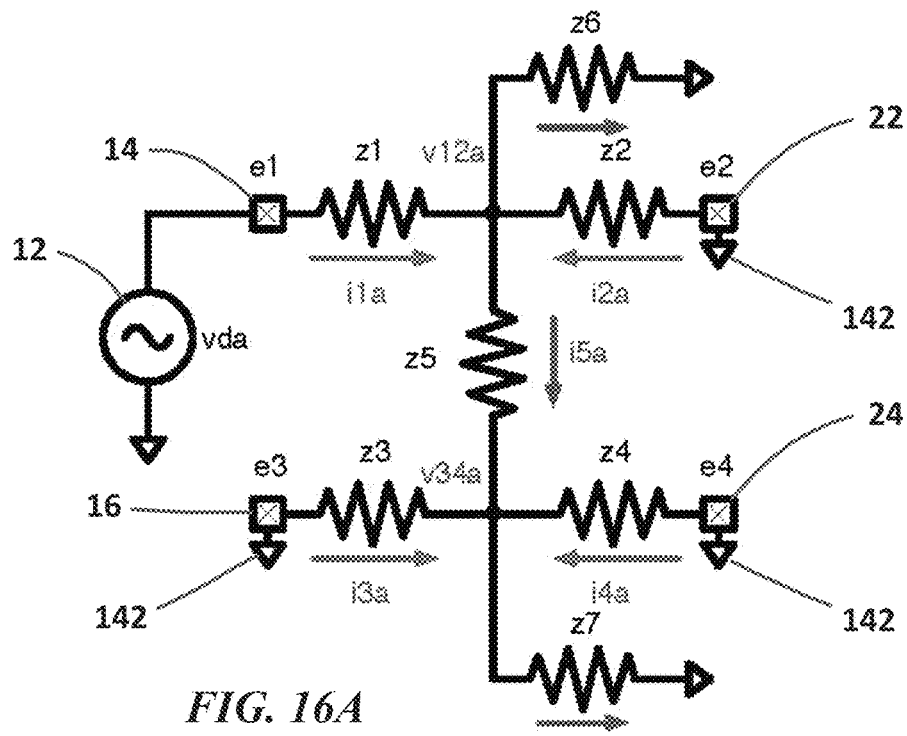
FIGS. 16A, 16B, 16C, and 16D schematically illustrate applied drive voltage configurations for measuring body impedance using an indefinite admittance matrix approach, in accordance with many embodiments.
Figure 16B:
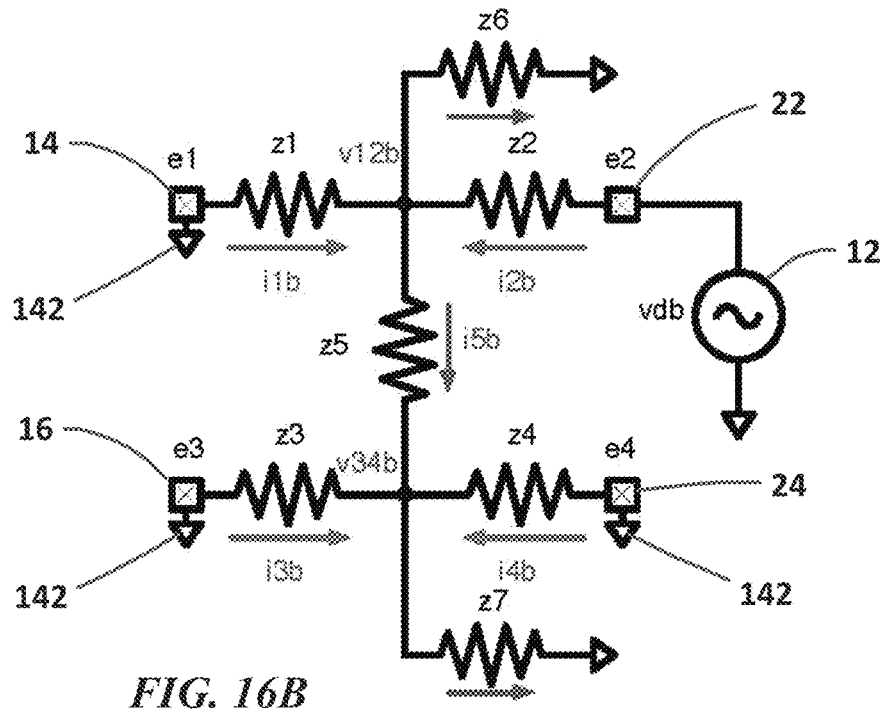
Figure 16C:
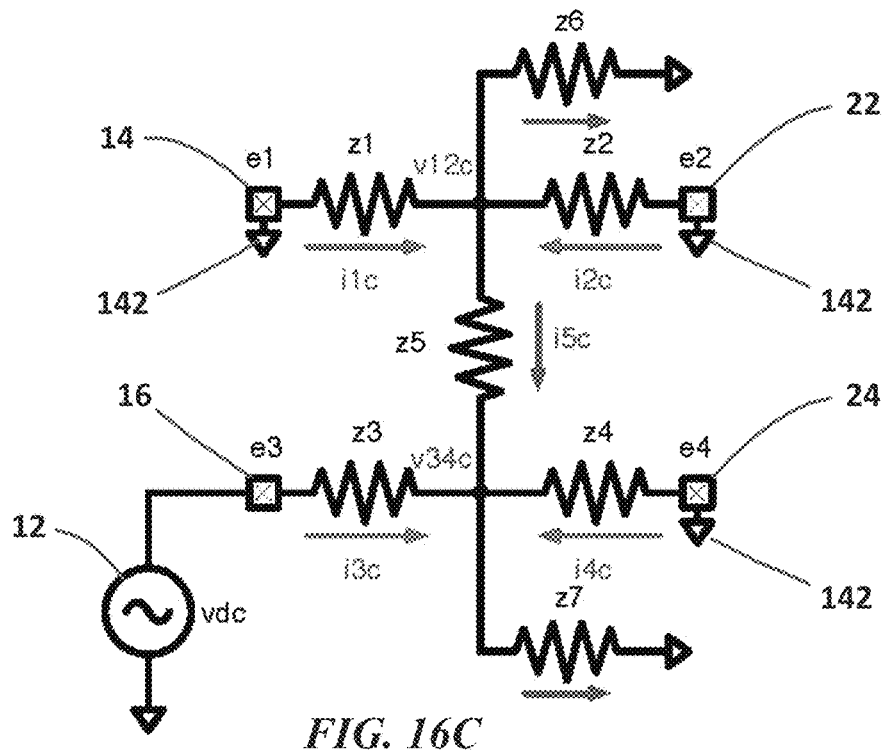
Figure 16D:
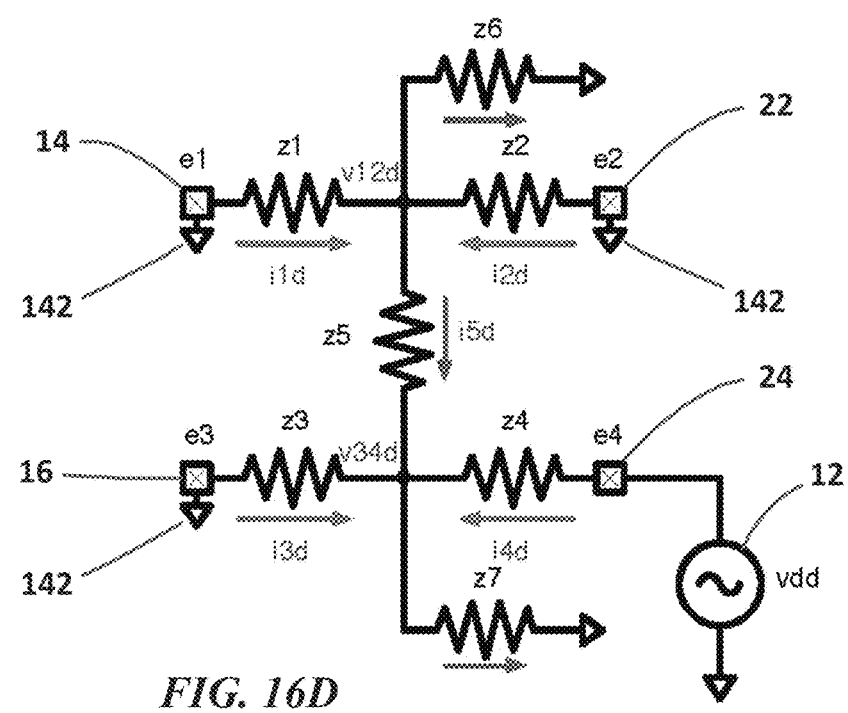

FIGS. 16A, 16B, 16C, and 16D schematically illustrate drive voltage configurations that can be used to measure body impedance using the indefinite admittance matrix approach. As shown in FIG. 16A, while maintaining contact between the subject 140 and the electrodes (e1, e2, e3, e4), the second, third, and fourth electrodes (e2, e3, e4) are connected to a ground voltage 142 and current (i1a, i2a, i3a, i4a) flowing through each of the electrodes (e1, e2, e3, e4) resulting from application of a first known voltage (vda) to the first electrode (e1) is measured while the second, third, and fourth electrodes (e2, e3, e4) are connected to the ground voltage 142. As shown in FIG. 16B, while maintaining contact between the subject 140 and the electrodes (e1, e2, e3, e4), the first, third, and fourth electrodes (e1, e3, e4) are connected to the ground voltage 142 and current (i1b, i2b, i3b, i4b) flowing through each of the electrodes (e1, e2, e3, e4) resulting from application of a second known voltage (vdb) to the second electrode (e2) is measured while the first, third, and fourth electrodes (e1, e3, e4) are connected to the ground voltage 142. As shown in FIG. 16C, while maintaining contact between the subject 140 and the electrodes (e1, e2, e3, e4), the first, second, and fourth electrodes (e1, e2, e4) are connected to the ground voltage 142 and current (i1c, i2c, i3c, i4c) flowing through each of the electrodes (e1, e2, e3, e4) resulting from application of a third known voltage (vdc) to the third electrode (e3) is measured while the first, second, and fourth electrodes (e1, e2, e4) are connected to the ground voltage 142. As shown in FIG. 16D, while maintaining contact between the subject 140 and the electrodes (e1, e2, e3, e4), the first, second, and third electrodes (e1, e2, e3) are connected to the ground voltage 142 and current (i1d, i2d, i3d, i4d) flowing through each of the electrodes (e1, e2, e3, e4) resulting from application of a fourth known voltage (vdd) to the fourth electrode (e3) is measured while the first, second, and third electrodes (e1, e2, e3) are connected to the ground voltage 142.

A body impedance value for the subject is calculated based on the applied voltages (vda, vdb, vdc, and vdd) and the corresponding resulting measured currents (i1a, i2a, i3a, i4a; i1b, i2b, i3b, i4b; i1c, i2c, i3c, i4c; i1d, i2d, i3d, i4d). While there may be other suitable ways to calculate the body impedance based on the applied voltages and the corresponding resulting measured currents, the approach described below can be used. The approach described herein includes: (1) calculation of the interface impedances (z1, z2, z3, z4), (2) using the calculated interface impedances to calculate the chassis impedances (z6, z7), and (3) using both the calculated interface impedances and the chassis impedances to calculate the body impedance (z5).

The interface impedances (z1, z2, z3, z4) can be calculated using equations (6), (7), (8), and (9).

$$z_1 = \frac{i_{2a}v_{db} + i_{2b}v_{da}}{i_{1a}i_{2b} - i_{1b}i_{2a}} \quad \text{equation (6)}$$

$$z_2 = \frac{i_{1a}v_{db} + i_{1b}v_{da}}{i_{1a}i_{2b} - i_{1b}i_{2a}} \quad \text{equation (7)}$$

$$z_3 = \frac{i_{4c}v_{dd} + i_{4d}v_{dc}}{i_{3c}i_{4d} - i_{3d}i_{4c}} \quad \text{equation (8)}$$

$$z_4 = \frac{i_{3c}v_{dd} + i_{3d}v_{dc}}{i_{3c}i_{4d} - i_{3d}i_{4c}} \quad \text{equation (9)}$$

Simulations have shown reduced error in the calculated body impedance (z5) when the equations used to calculate the body impedance (z5) are selected to avoid use of the lowest of the calculated interface impedance (z1, z2, z3, or z4). When z1 is the lowest of the calculated interface impedances (z1, z2, z3, z4), equations (10) and (11) (which do not use z1) can be used to calculate the body impedance (z5).

$$z_7 = \frac{z_3(-i_{1b}i_{3d} + i_{1d}i_{3b})}{i_{1b}i_{2d} + i_{1b}i_{3d} + i_{1b}i_{4d} - i_{1d}i_{2d} - i_{1d}i_{3b} - i_{1d}i_{4b}} \quad \text{equation (10)}$$

$$z_5 = \frac{z_7(i_{2c}z_2 - i_{4c}z_4)}{i_{3c}z_7 + i_{4c}z_4 + i_{4c}z_7} \quad \text{equation (11)}$$

When z2 is the lowest of the calculated interface impedances (z1, z2, z3, z4), equations (12) and (13) (which do not use z2) can be used to calculate the body impedance (z5).

$$z_7 = \frac{z_4(i_{2a}i_{4c} - i_{2c}i_{4a})}{i_{1a}i_{2c} - i_{1c}i_{2a} - i_{2a}i_{3c} - i_{2a}i_{4c} + i_{2c}i_{3a} + i_{2c}i_{4a}} \quad \text{equation (12)}$$

$$z_5 = \frac{z_7(i_{1d}z_1 - i_{3d}z_3)}{i_{3d}z_3 + i_{3d}z_7 + i_{4d}z_7} \quad \text{equation (13)}$$

When z3 is the lowest of the calculated interface impedances (z1, z2, z3, z4), equations (14) and (15) (which do not use z3) can be used to calculate the body impedance (z5).

$$z_6 = \frac{z_1(-i_{1b}i_{3d} + i_{1d}i_{3b})}{i_{1b}i_{3d} - i_{1d}i_{3b} + i_{2b}i_{3d} - i_{2d}i_{3b} - i_{3b}i_{4d} + i_{3d}i_{4b}} \quad \text{equation (14)}$$

$$z_5 = \frac{z_6(-i_{2a}z_2 + i_{4a}z_4)}{i_{1a}z_6 + i_{2a}z_2 + i_{2a}z_6} \quad \text{equation (15)}$$

When z4 is the lowest of the calculated interface impedances (z1, z2, z3, z4), equations (16) and (17) (which do not use z4) can be used to calculate the body impedance (z5).

$$z_6 = \frac{z_2(-i_{2a}i_{4c} + i_{2c}i_{4a})}{i_{1a}i_{4c} - i_{1c}i_{4a} + i_{2a}i_{4c} - i_{2c}i_{4a} + i_{3a}i_{4c} + i_{3c}i_{4a}} \quad \text{equation (16)}$$

$$z_5 = \frac{z_6(-i_{1b}z_1 - i_{3d}z_3)}{i_{1b}z_1 + i_{1b}z_6 + i_{2b}z_6} \quad \text{equation (17)}$$

Figure 17:
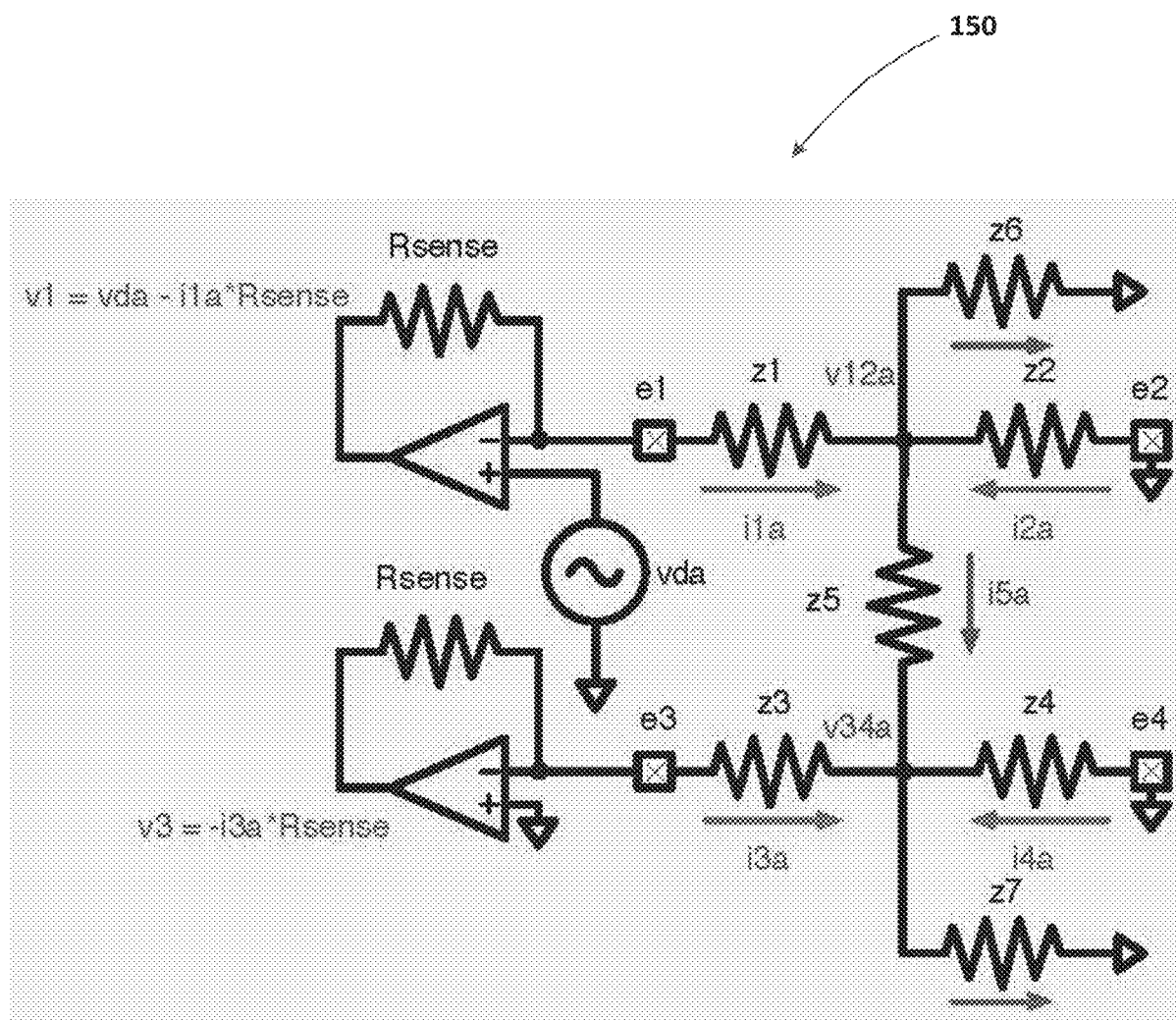
FIGS. 17, 18, and 19 schematically illustrate example sense amplifier implementations for measuring currents in an indefinite matrix approach for measuring body impedance, in accordance with many embodiments.
Figure 18:
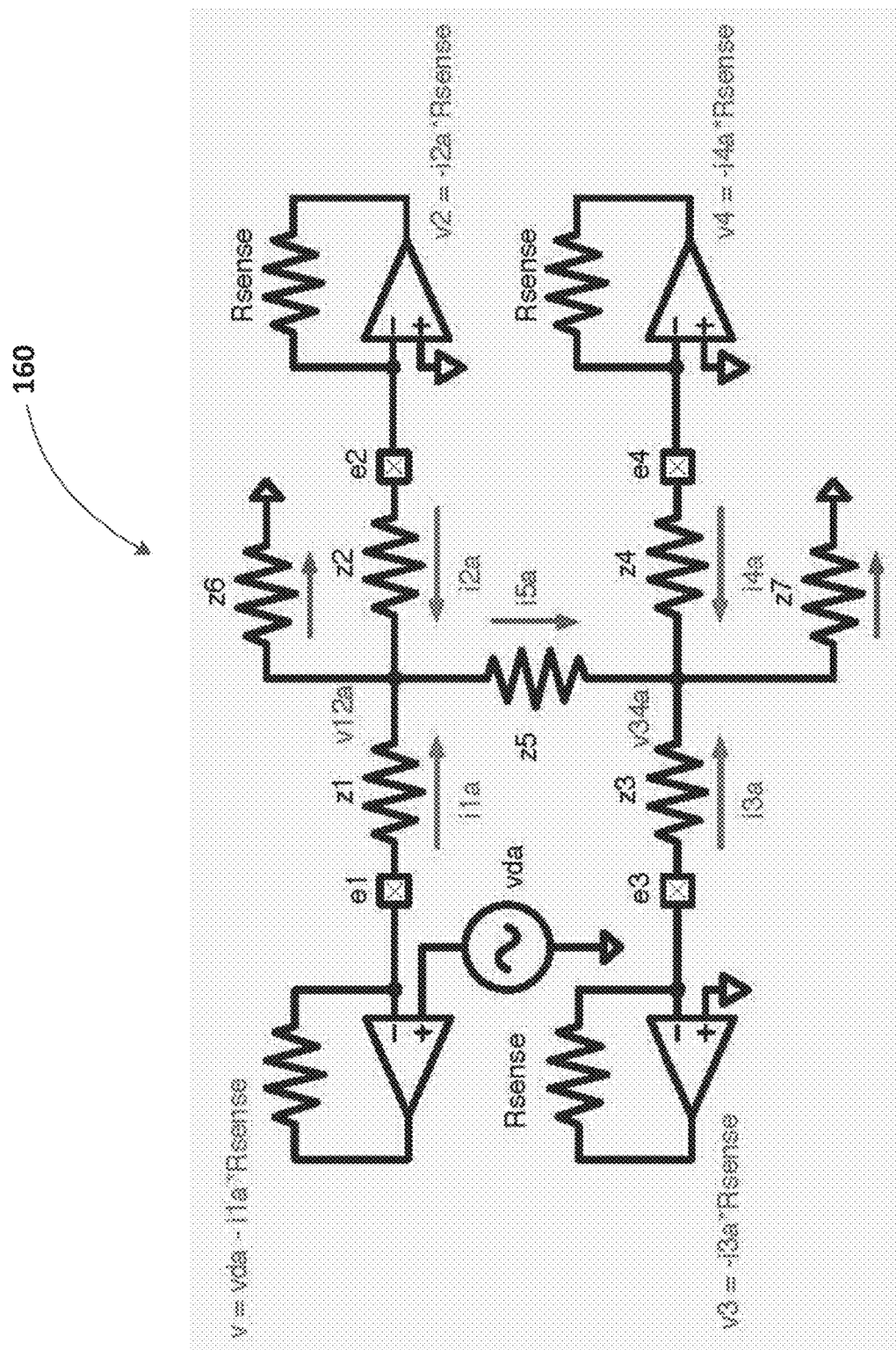
Figure 19:
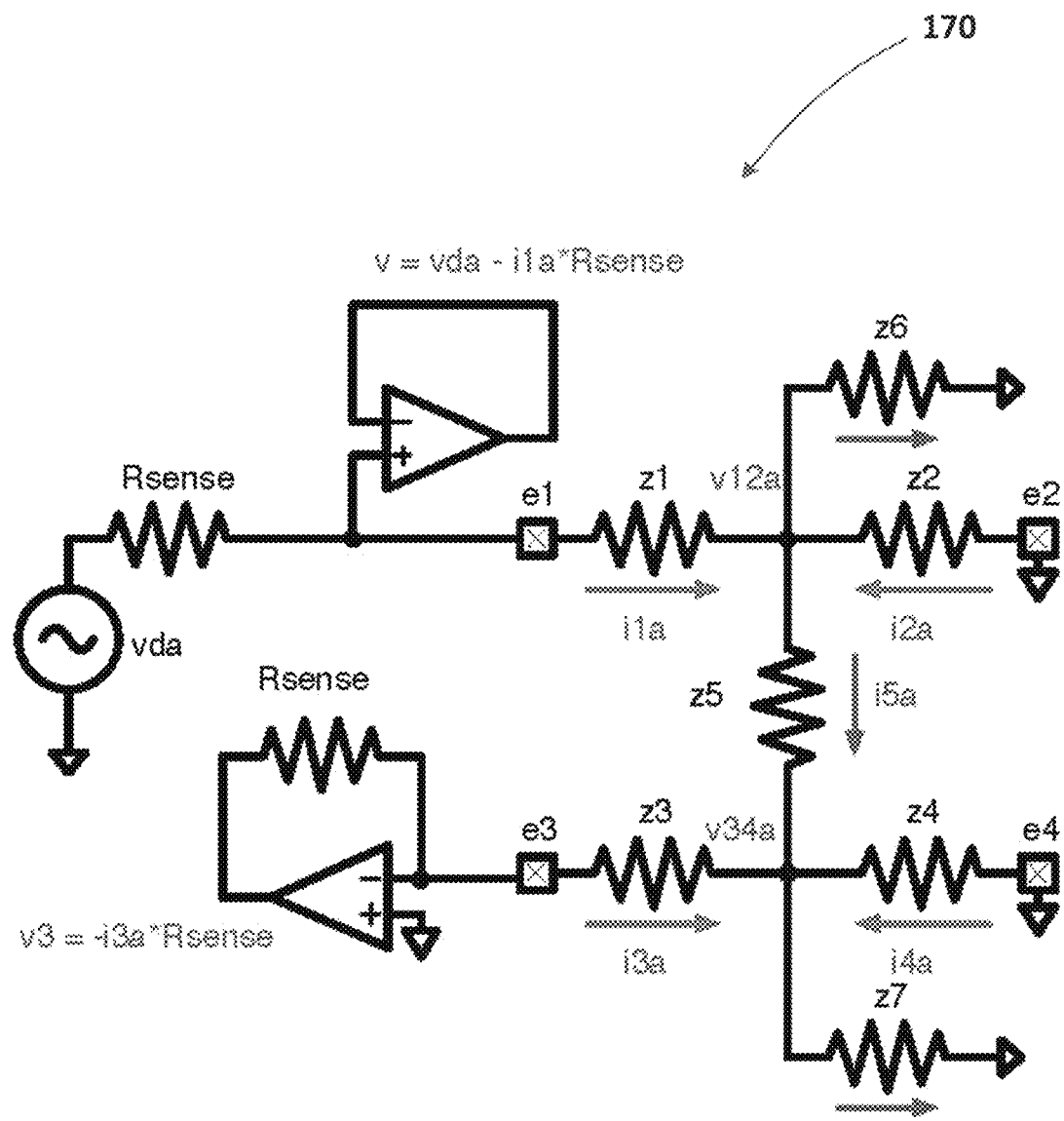

FIGS. 17, 18, and 19 schematically illustrate example usages of sense amplifiers for measuring the currents (i1a, i2a, i3a, i4a; i1b, i2b, i3b, i4b; i1c, i2c, i3c, i4c; i1d, i2d, i3d, i4d). FIG. 17 illustrates an implementation 150 that employs two TIAs, with one of the TIAs being driven with voltage and the other TIA being shorted to the ground reference voltage. The output of the TIAs is proportional to current. The two TIAs can be moved around to cover the 12 different combinations. For example, each of the two TIAs can be connected to two different sensing electrodes via a switching assembly operable to selectively connect each TIA to either one of the two locations. FIG. 18 illustrates an implementation 160 that employs four TIAs. The use of four TIAs allows for measurement of all four currents at the same time. The use of four TIAs reduces the number of different switched combinations down to four. Switching between the four different combinations can be made at the TIA positive input instead of the electrodes, therefore the parasitics remain the same. FIG. 19 illustrates an implementation 170 that does not drive a TIA. Instead, in the illustrated combination, the electrode e1 is driven through the resistor (Rsense). Therefore, only one TIA would be required for a lean implementation.

Figure 20:
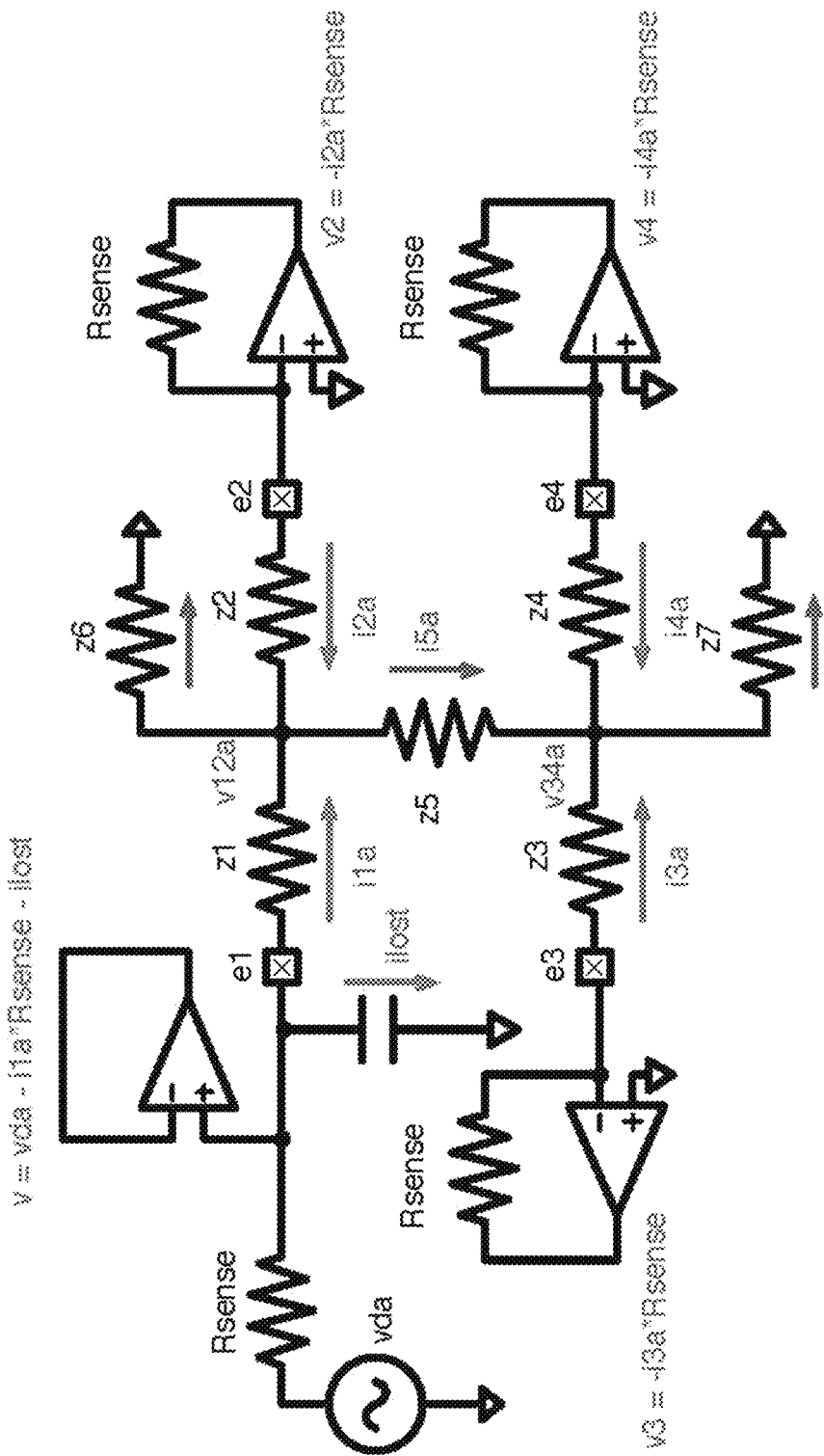
FIG. 20 schematically illustrates a parasitic current that may induce error in an indefinite matrix approach for measuring body impedance, in accordance with many embodiments.
Figure 21:
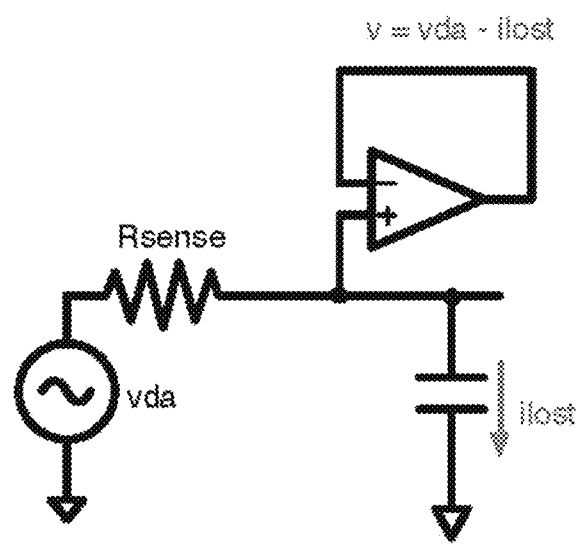
FIG. 21 schematically illustrates an approach for measuring a parasitic current in an indefinite matrix approach for measuring body impedance, in accordance with many embodiments.

FIG. 20 schematically illustrates a parasitic current (ilost) that may induce error in an indefinite matrix approach for measuring body impedance, in accordance with many embodiments. If the parasitic current at the driven electrode (ilost) is significant, the parasitic current (ilost) may impact the measured currents. FIG. 21 schematically illustrates an approach for measuring the parasitic current (ilost) in which the electrode (e.g., e1) is disconnected either directly or by no contact between the electrode and the subject and the parasitic current (ilost) is measured during the application of the applied voltage (e.g., vda). The measured parasitic current is then subtracted from the measured current to generate a corrected current, which can then be used to calculate the body impedance (z5). The parasitic current at each of the electrodes and a corresponding corrected current can be used in any suitable combination for calculating the body impedance (z5).

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., blood pressure measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

While the exemplary embodiments have been described in some detail, by way of example and for clarity of understanding, those of skill in the art will recognize that a variety of modifications, adaptations, and changes may be employed.

What is claimed is:

1. A wrist-worn device for measuring a body impedance of a user, the wrist-worn device comprising:
   a housing configured to be worn on a user's wrist;
   electrodes comprising:
      a first electrode coupled with the housing and oriented to engage the user's wrist when the wrist-worn device is worn on the user's wrist;
      a second electrode coupled with the housing and oriented to engage the user's wrist when the wrist-worn device is worn on the user's wrist;
      a third electrode coupled with the housing and oriented for engagement by a first finger on an arm of the user opposite to an arm of the user having the wrist on which the wrist-worn device is worn; and
      a fourth electrode coupled with the housing and oriented for engagement by a second finger on the arm of the user opposite to the arm of the user having the wrist on which the wrist-worn device is worn; and
   a control unit operatively coupled with the first, second, third, and fourth electrodes, the control unit being configured to:
      propagate an alternating drive current through the user between first and second drive current electrodes of the electrodes so as to maintain a voltage level of a first sense electrode of the electrodes relative to a reference ground voltage level via a feedback loop that is operatively connected between one of the drive current electrodes and the first sense electrode;
      sense one or more voltage levels of the user resulting from the alternating drive current via the first sense electrode and a second sense electrode of the electrodes; and
      calculate a body impedance of the user based on the alternating drive current and the one or more sensed voltage levels.

2. The wrist-worn device of claim 1, wherein the feedback loop includes an integrator having an integrator first input connected with the first sense electrode, an integrator second input connected to a ground having the reference ground voltage level, and an integrator output that outputs a voltage level lower than the reference ground voltage level when the first sense electrode has a voltage level higher than the reference ground voltage level.

3. The wrist-worn device of claim 2, wherein the feedback loop includes a trans impedance amplifier (TIA) having a TIA first input connected to the integrator output, a TIA output, and a TIA second input connected with the TIA output; the TIA second input being connected to said one of the drive electrodes.

4. The wrist-worn device of claim 3, wherein the feedback loop includes:
   a first resistor connected between the first sense electrode and the integrator first input;
   a capacitor connected between the integrator first input and the integrator output; and
   a second resister connected between the TIA output and the TIA second input.

5. The wrist-worn device of claim 1, comprising an external case in contact with the user when the wrist-worn device is worn by the user, the external case being connected to a ground having the reference ground voltage level.

6. The wrist-worn device of claim 5, comprising circuitry at least partially disposed within the external case, and wherein:

the external case is configured to be worn on the wrist;
the first and second drive current electrodes are mounted on the external case; and
the first and second sense electrodes are mounted on the external case.

7. The wrist-worn device of claim 5, configured to maintain a predetermined portion of the user at the reference ground voltage level while the predetermined portion of the user is contacted by at least one of the first drive current electrode, the second drive current electrode, the first sense electrode, and the second sense electrode.

8. A wrist-worn device for measuring a body impedance of a user, the wrist-worn device comprising:
a housing configured to be worn on a user's wrist;
electrodes comprising:
a first electrode coupled with the housing and oriented to engage the user's wrist when the wrist-worn device is worn on the user's wrist;
a second electrode coupled with the housing and oriented to engage the user's wrist when the wrist-worn device is worn on the user's wrist;
a third electrode coupled with the housing and oriented for engagement by a first finger on an arm of the user opposite to an arm of the user having the wrist on which the wrist-worn device is worn; and
a fourth electrode coupled with the housing and oriented for engagement by a second finger on the arm of the user opposite to the arm of the user having the wrist on which the wrist-worn device is worn; and
a control unit operatively coupled with the first, second, third, and fourth electrodes, the control unit being configured to:
(a) propagate an alternating drive current through the user between first and second drive current electrodes of the electrodes;
(b) connect a known capacitance to input nodes of a sense amplifier, the input nodes of the sense amplifier being connected to first and second sense electrodes, of the electrodes, used to sense voltage levels of the user resulting from the alternating drive current;
(c) measure a voltage differential between the input nodes of the sense amplifier while the known capacitance is connected to the input nodes of the sense amplifier;
(d) repeat (b) and (c) a plurality of times with different values of capacitance connected to the input nodes of the sense amplifier; and
(e) calculate the body impedance value based on the alternating drive current and the measured voltage differentials between the input nodes of the sense amplifier for the different known capacitances connected to the input nodes of the sense amplifier.

9. The wrist-worn device of claim 8, wherein (b) and (c) are accomplished at least five times using five different values of known capacitance connected to the input nodes of the sense amplifier.

10. The wrist-worn device of claim 8, wherein the body impedance is calculated from the alternating drive current and the measured voltage differentials using an iterative approach.

11. The wrist-worn device of claim 8, configured to calculate impedance values for the sense electrodes and respective contact impedance for each of the first and second sense electrodes.

12. The wrist-worn device of claim 8, comprising an external case in contact with the user when the wrist-worn device is worn by the user, the external case being connected to a ground, the known capacitances being connected between at least one of the input nodes of the sense amplifier and the ground.

13. A wrist-worn device for measuring a body impedance of a user, the wrist-worn device comprising:
a housing configured to be worn on a user's wrist;
electrodes comprising:
a first electrode coupled with the housing and oriented to engage the user's wrist when the wrist-worn device is worn on the user's wrist;
a second electrode coupled with the housing and oriented to engage the user's wrist when the wrist-worn device is worn on the user's wrist;
a third electrode coupled with the housing and oriented for engagement by a first finger on an arm of the user opposite to an arm of the user having the wrist on which the wrist-worn device is worn; and
a fourth electrode coupled with the housing and oriented for engagement by a second finger on the arm of the user opposite to the arm of the user having the wrist on which the wrist-worn device is worn; and
a control unit operatively coupled with the first, second, third, and fourth electrodes, the control unit being configured to:
propagate an alternating drive current through the user between first and second drive current electrodes of the electrodes;
generate a first voltage signal via a first sense electrode, of the electrodes, contacted with the user;
generate a feedback voltage in response to the first voltage signal for application to a capacitor electrically coupled to the first sense electrode to reduce the effect of a parasitic impedance on the first voltage signal of the first sense electrode;
apply the feedback voltage to the capacitor;
generate a second voltage signal via a second sense electrode, of the electrodes, contacted with the user; and
calculate the body impedance of the user based on the drive current and the first and second voltage signals.

14. The wrist-worn device of claim 13, wherein the generation of the feedback voltage comprises amplification of the first voltage signal.

15. The wrist-worn device of claim 14, configured to control amplification of the first voltage signal using an automated approach so as to reduce error caused by parasitic impedance on the body impedance measurement.

16. The wrist-worn device of claim 15, configured to control the amount of capacitance of the capacitor connected to the first sense electrode using an automated approach so as to reduce error caused by parasitic impedance on the body impedance measurement.

17. The wrist-worn device of claim 14, configured to control the amount of capacitance of the capacitor connected to the first sense electrode using an automated approach so as to reduce error caused by parasitic impedance on the body impedance measurement.

18. The wrist-worn device of claim 13, comprising an external case in contact with the user when the wrist-worn device is worn by the user, the external case being connected to a ground voltage for the wrist-worn device.

19. A wrist-worn device for measuring a body impedance of a user, the wrist-worn device comprising:

a housing configured to be worn on a user's wrist;
electrodes comprising:
  a first electrode coupled with the housing and oriented to engage the user's wrist when the wrist-worn device is worn on the user's wrist;
  a second electrode coupled with the housing and oriented to engage the user's wrist when the wrist-worn device is worn on the user's wrist;
  a third electrode coupled with the housing and oriented for engagement by a first finger on an arm of the user opposite to an arm of the user having the wrist on which the wrist-worn device is worn; and
  a fourth electrode coupled with the housing and oriented for engagement by a second finger on the arm of the user opposite to the arm of the user having the wrist on which the wrist-worn device is worn; and
a control unit operatively coupled with the first, second, third, and fourth electrodes, the control unit being configured to:
  connect the second, third, and fourth electrodes to a ground voltage and measure current flowing through each of the first, second, third, and fourth electrodes resulting from application of a first known voltage to the first electrode while the second, third, and fourth electrodes are connected to the ground voltage;
  connect the first, third, and fourth electrodes to the ground voltage and measure current flowing through each of the first, second, third, and fourth electrodes resulting from application of a second known voltage to the second electrode while the first, third, and fourth electrodes are connected to the ground voltage;
  connect the first, second, and fourth electrodes to the ground voltage and measure current flowing through each of the first, second, third, and fourth electrodes resulting from application of a third known voltage to the third electrode while the first, second, and fourth electrodes are connected to the ground voltage;
  connect the first, second, and third electrodes to the ground voltage and measure current flowing through each of the first, second, third, and fourth electrodes resulting from application of a fourth known voltage to the fourth electrode while the first, second, and third electrodes are connected to the ground voltage; and
  calculate the body impedance value for the user based on the applied voltages and the measured currents.

20. The wrist-worn device of claim 19, wherein the first, second, third, and fourth applied voltages are substantially equal in magnitude.

21. The wrist-worn device of claim 19, configured to:
measure a first parasitic current with the first electrode not connected with the user while applying the first known voltage to the first electrode; and
calculate a corrected first current for the first electrode resulting from the application of the first known voltage to the first electrode by subtracting the first parasitic current from the current measured through the first electrode while the first known voltage is applied to the first electrode and the first electrode is connected with the user, and
wherein the body impedance value is calculated based in part on the corrected first current.

22. The wrist-worn device of claim 21, configured to:
measure a second parasitic current with the second electrode not connected with the user while applying the second known voltage to the second electrode;
calculate a corrected second current for the second electrode resulting from the application of the second known voltage to the second electrode by subtracting the second parasitic current from the current measured through the second electrode while the second known voltage is applied to the second electrode and the second electrode is connected with the user;
measure a third parasitic current with the third electrode not connected with the user while applying the third known voltage to the third electrode;
calculate a corrected third current for the third electrode resulting from the application of the third known voltage to the third electrode by subtracting the third parasitic current from the current measured through the third electrode while the third known voltage is applied to the third electrode and the third electrode is connected with the user;
measure a fourth parasitic current with the fourth electrode not connected with the user while applying the fourth known voltage to the fourth electrode; and
calculate a corrected fourth current for the fourth electrode resulting from the application of the fourth known voltage to the fourth electrode by subtracting the fourth parasitic current from the current measured through the fourth electrode while the fourth known voltage is applied to the fourth electrode and the fourth electrode is connected with the user, and
wherein the body impedance value is calculated based in part on the corrected second current, the corrected third current, and the corrected fourth current.

* * * * *